United States Patent
Gysling et al.

(10) Patent No.: US 7,058,549 B2
(45) Date of Patent: Jun. 6, 2006

(54) APPARATUS AND METHOD FOR MEASURING UNSTEADY PRESSURES WITHIN A LARGE DIAMETER PIPE

(75) Inventors: Daniel L. Gysling, Glastonbury, CT (US); Douglas H. Loose, Southington, CT (US); Robert Maron, Middletown, CT (US); Thomas Engel, East Hampton, CT (US); Paul Croteau, Columbia, CT (US)

(73) Assignee: CIDRA Corporation, Wallingford, CT (US)

( * ) Notice: Subject to any disclaimer, the term of this patent is extended or adjusted under 35 U.S.C. 154(b) by 0 days.

(21) Appl. No.: 10/762,408

(22) Filed: Jan. 21, 2004

(65) Prior Publication Data

US 2004/0226386 A1    Nov. 18, 2004

Related U.S. Application Data

(60) Provisional application No. 60/482,515, filed on Jun. 24, 2003, provisional application No. 60/441,652, filed on Jan. 22, 2003, provisional application No. 60/441,395, filed on Jan. 21, 2003, provisional application No. 60/441,373, filed on Jan. 21, 2003.

(51) Int. Cl.
    G06F 19/00    (2006.01)
    G06F 1/20     (2006.01)

(52) U.S. Cl. ............... 702/189; 702/45; 702/48; 73/861; 73/861.18; 73/861.22

(58) Field of Classification Search ........ 702/189, 702/45, 47, 48, 50, 52, 54; 73/861, 753, 73/861.18, 861.42, 227, 53.01, 61.41, 61.45, 73/61.47, 61.49, 64.53, 570, 645
See application file for complete search history.

(56) References Cited

U.S. PATENT DOCUMENTS

| 4,048,853 A | 9/1977 | Smith et al. ............. 73/861.25 |
| 4,080,837 A | 3/1978 | Alexander et al. ......... 73/61.45 |
| 4,248,085 A | 2/1981 | Coulthard ................ 73/861.06 |
| 4,445,389 A | 5/1984 | Potzick et al. ........... 73/861.27 |
| 4,896,540 A | 1/1990 | Shakkottai et al. ....... 73/861.02 |
| 5,040,415 A | 8/1991 | Barkhoudarian ......... 73/861.03 |
| 5,083,452 A | 1/1992 | Hope ......................... 73/61 R |
| 5,218,197 A | 6/1993 | Carroll ................. 250/227.19 |

(Continued)

FOREIGN PATENT DOCUMENTS

WO    93/14382    7/1993

(Continued)

OTHER PUBLICATIONS

"Noise and Vibration Control Engineering Principles and Applications", Leo L. Beranek and Istvan L. Ver, A. Wiley Interscience Publication, pp. 537-541, Aug. 1992.

(Continued)

Primary Examiner—Patrick J. Assouad

(57) ABSTRACT

An apparatus 10 is provided that includes a spatial array of at least two unsteady pressure sensors 18–21 placed at predetermined axial locations $x_1$–$x_N$ disposed axially along a pipe 14 for measuring at least one parameter of a fluid 12 flowing in the pipe 14. The pressure sensors 18–21 comprise a plurality of pressure sensing elements such as piezoelectric film sensors 23 for measuring unsteady pressures associated with acoustical pressures and/or vortical disturbances. The sensing elements are disposed circumferentially around the pipe and spaced a predetermined distance. The pressure signals $P_1(t)$–$P_N(t)$ provided by the pressure sensors 18–21 are processed by a processing unit to provide an output signal indicative of a parameter of the fluid.

40 Claims, 24 Drawing Sheets

U.S. PATENT DOCUMENTS

| | | | |
|---|---|---|---|
| 5,285,675 A | 2/1994 | Colgate et al. | 73/23.2 |
| 5,355,083 A * | 10/1994 | George et al. | 324/229 |
| 5,367,911 A | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,526,844 A | 6/1996 | Kamen et al. | 137/614.11 |
| 5,541,510 A * | 7/1996 | Danielson | 324/233 |
| 5,591,922 A | 1/1997 | Segeral et al. | 73/861.04 |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,948,959 A | 9/1999 | Peloquin | 73/1.83 |
| 6,016,702 A | 1/2000 | Maron | 73/705 |
| 6,151,958 A | 11/2000 | Letton et al. | 73/61.79 |
| 6,202,494 B1 | 3/2001 | Riebel et al. | 73/861.29 |
| 6,354,147 B1* | 3/2002 | Gysling et al. | 73/61.79 |
| 6,862,920 B1* | 3/2002 | Gysling et al. | 73/61.79 |
| 6,378,357 B1 | 4/2002 | Han et al. | 73/54.41 |
| 6,435,030 B1 | 8/2002 | Gysling et al. | 73/587 |
| 6,443,226 B1 | 9/2002 | Diener et al. | 166/241.6 |
| 6,450,037 B1* | 9/2002 | McGuinn et al. | 73/705 |
| 6,463,813 B1* | 10/2002 | Gysling | 73/862.59 |
| 6,536,291 B1 | 3/2003 | Gysling et al. | 73/861.42 |
| 6,550,342 B1 | 4/2003 | Croteau et al. | 73/800 |
| 6,558,036 B1 | 5/2003 | Gysling et al. | 374/147 |
| 6,587,798 B1* | 7/2003 | Kersey et al. | 702/50 |
| 6,601,458 B1 | 8/2003 | Gysling et al. | 73/861.04 |
| 6,609,069 B1 | 8/2003 | Gysling | 702/48 |
| 6,691,584 B1* | 2/2004 | Gysling et al. | 73/861.42 |
| 6,698,297 B1 | 3/2004 | Gysling | 73/861.63 |
| 6,732,575 B1* | 5/2004 | Gysling et al. | 73/61.79 |
| 6,782,150 B1 | 8/2004 | Davis et al. | 385/12 |
| 6,813,962 B1 | 11/2004 | Gysling et al. | 73/861.26 |
| 6,837,098 B1 | 1/2005 | Gysling et al. | 73/61.79 |
| 6,868,737 B1 | 3/2005 | Croteau et al. | 73/800 |
| 6,889,562 B1* | 5/2005 | Gysling et al. | 73/861.42 |
| 6,898,541 B1 | 5/2005 | Gysling et al. | 702/100 |
| 2002/0095263 A1 | 7/2002 | Gysling et al. | |
| 2002/0100327 A1* | 8/2002 | Kersey et al. | 73/597 |
| 2002/0123852 A1 | 9/2002 | Gysling et al. | |
| 2002/0129662 A1* | 9/2002 | Gysling et al. | 73/861.42 |
| 2002/0134144 A1* | 9/2002 | Gysling et al. | 73/61.79 |
| 2002/0152802 A1* | 10/2002 | Gysling et al. | 73/61.79 |
| 2002/0194932 A1* | 12/2002 | Gysling et al. | 73/861.42 |
| 2003/0038231 A1* | 2/2003 | Bryant et al. | 250/227.14 |
| 2003/0066359 A1* | 4/2003 | Gysling et al. | 73/861.23 |
| 2003/0084707 A1* | 5/2003 | Gysling | 73/32 A |
| 2003/0089161 A1* | 5/2003 | Gysling | 73/32 A |
| 2003/0136186 A1* | 7/2003 | Gysling | 73/64.53 |
| 2003/0154036 A1* | 8/2003 | Gysling | 702/25 |
| 2004/0016284 A1 | 1/2004 | Gysling et al. | |
| 2004/0069069 A1 | 4/2004 | Croteau et al. | |
| 2004/0074312 A1* | 4/2004 | Gysling | 73/861.04 |
| 2004/0144182 A1* | 7/2004 | Gysling | 73/861.42 |
| 2004/0167735 A1 | 8/2004 | Rothman et al. | |
| 2004/0168523 A1* | 9/2004 | Fernald et al. | 73/861.01 |
| 2004/0182139 A1* | 9/2004 | Gysling et al. | 73/61.79 |
| 2004/0194539 A1* | 10/2004 | Gysling | 73/61.45 |
| 2004/0199340 A1* | 10/2004 | Kersey et al. | 702/50 |
| 2004/0210404 A1* | 10/2004 | Gysling et al. | 702/50 |
| 2004/0255695 A1* | 12/2004 | Gysling et al. | 73/862 |
| 2005/0000289 A1* | 1/2005 | Gysling et al. | 73/645 |
| 2005/0005712 A1* | 1/2005 | Gysling et al. | 73/861.23 |
| 2005/0005713 A1* | 1/2005 | Winston et al. | 73/861.42 |
| 2005/0011258 A1* | 1/2005 | Gysling et al. | 73/195 |
| 2005/0011283 A1* | 1/2005 | Gysling et al. | 73/861.44 |
| 2005/0011284 A1* | 1/2005 | Gysling et al. | 73/861.44 |
| 2005/0033545 A1* | 2/2005 | Gysling | 702/138 |
| 2005/0039520 A1* | 2/2005 | Davis et al. | 73/49.5 |
| 2005/0050956 A1* | 3/2005 | Gysling et al. | 73/753 |
| 2005/0072216 A1* | 4/2005 | Engel | 73/53.01 |

FOREIGN PATENT DOCUMENTS

| | | |
|---|---|---|
| WO | WO 99/067629 | 12/1999 |
| WO | 02/95263 | 1/2001 |

OTHER PUBLICATIONS

"Two Decades of Array Signal Processing Research", The Parametric Approach, H. Krim and M. Viberg, IEEE Signal Processing Magazine, Jul., 1996, pp.67-94.

"Development of an array of pressure sensors with PVDF film, Experiments in Fluids 26", Jan. 8, 1990, Springer-Verlag.

"Viscous Attentuation of Acoustic Waves in Suspensions" by R.L. Gibson, Jr. and M.N. Toksoz.

Piezo Film Sensors Technical Manual-Provided by Measurement Specialties, Inc.

Sonar-Based Volumetric Flow Meter For Pulp and Paper Applications-Daniel L. Gysling & Douglas H. Loose-Dec. 13, 2003.

Sonar-Based Volumetric Flow Meter for Chemical and Petrochemical Applications-Daniel L. Gysling & Douglas H. Loose-Feb. 14, 2003.

New Flowmeter Principle-By Walt Boyes-Flow Control Magazine-Oct. 2003 Issue.

SONAR Gets into the Flow-Daniel L. Gysling and Douglas H. Loose-Modern Process-Jan. 2004.

* cited by examiner

APPARATUS AND METHOD FOR MEASURING UNSTEADY PRESSURES WITHIN A LARGE DIAMETER PIPE

CROSS-REFERENCE TO RELATED APPLICATIONS

This application claims the benefit of U.S. Provisional Patent Application No. 60/482,515 filed Jun. 24, 2003, U.S. Provisional Patent Application No. 60/441,652 filed Jan. 22, 2003, U.S. Provisional Patent Application No. 60/441,395 filed Jan. 21, 2003, U.S. Provisional Patent Application No. 60/441,373 filed Jan. 21, 2003, which are all incorporated herein by reference.

TECHNICAL FIELD

This invention relates to apparatus for measuring and determining parameters of a homogeneous or non-homogeneous fluid flowing within a pipe or conduit, and more particularly to apparatus for measuring unsteady pressures created by acoustic disturbances and/or vortical disturbances of fluid within a large diameter pipe to determine parameters of the flowing fluid.

BACKGROUND ART

Numerous technologies have been implemented to measure volumetric and mass flow rates of fluids in industrial processes. Some of the more common approaches are based upon ultrasonic time of flight and/or Doppler effects, Coriolis effects, rotating wheels, electromagnetic induction, and pressure differentials. Each of these techniques has certain drawbacks. For example, invasive techniques that rely on insertion of a probe into the flow, or geometry changes in the pipe, may be disruptive to the process and prone to clogging. Other methods such as ultrasonics may be susceptible to air or stratified flow. Meters that use rotating wheels or moving parts are subject to reliability issues. Coriolis meters are limited when pipe diameters become large due to the increase in force required to vibrate the pipe.

One such process fluid is a saturated vapor/liquid fluid mixture (e.g., steam). It would be advantageous to be able to measure the vapor quality of this fluid mixture. Vapor quality of a saturated vapor/liquid mixture is defined as ratio of the mass of the vapor phase to the total mass of the mixture. Saturated mixtures exist at temperatures and pressures at which liquid and vapor phases coexist. The temperatures and pressures at which the liquid and vapor phases coexist lie under the "vapor bubble" on a phase diagram. The collection of points known as the saturated liquid line and the collections of points known as the saturated vapor line define the vapor bubble. These two lines connect at, what is tenned, the critical point. Saturated mixtures exist only under the vapor bubble. For pressures and temperatures outside of the vapor bubble, the fluid exists as a single phase and the properties of that fluid, such as density, enthalpy, internal energy, etc., are uniquely defined by the pressure and temperature. For common fluids, such as water, these properties are tabulated as functions of pressure and temperatures and are available through a variety of references.

For fluids at pressures and temperatures that lie within the vapor bubble, the fluids represent mixtures of the liquid and vapor phase. Although the properties of both the vapor and liquid phases are well defined (and tabulated for known substances), the properties of the mixture are no longer uniquely defined as functions of pressure and temperature.

In order to define the averaged properties of a saturated mixture, the ratio of the vapor and liquid components of the mixture must be defined. The quality of the mixture, in addition to the pressure and temperature, must be defined to uniquely determine the properties of the mixture.

Measuring the average properties of a mixture is important in many industrial application since it is the mass averaged properties of the working fluid that enter directly into monitoring the thermodynamic performance of many processes. For example, it is the difference in the flux of enthalpy of the steam mixture flowing into and exiting from a turbine that determines the maximum mechanical work that can be extracted from the working fluid, and thus is critical to determining component efficiency. However, if the steam entering or exiting the turbine were saturated, pressure and temperature measurement would not sufficient to determine the specific enthalpy, but rather, a measure of the quality of the steam would be required to uniquely define the thermodynamic properties of the saturated steam mixture.

Note that once the quality and pressure (or temperature) of a saturated mixture is defined, the thermodynamic properties of the mixture are defined through mixing laws provided the properties of the liquid and vapor sates are known. For example, measuring speed of sound enables one to determine quality, which in turn enables one to calculate enthalpy, density, and other properties of the mixture. In addition to measuring the specific enthalpy, a measurement of the total mass is also, in general, required to determine the flux of enthalpy.

There are many other situations where knowing the quality of a saturated mixture is beneficial. For example, in a steam power plant, the quality of the steam within the steam turbine affects blade life. Generally it is desired to operate so the quality is as high as possible throughout the turbine to minimize liquid water drops that will erode the metal blades. Knowing the quality at the turbine inlet and exhaust (or at the exhaust only if the inlet is super-heated) provides a means to monitor the quality throughout the turbine. Also, to monitor plant performance so that it can be operated at optimum conditions and to identify degradation effects, the steam turbine thermal performance must be known. This requires the fluid enthalpy at the inlet and exhaust of each turbine to be known. If the fluid at either or both locations is saturated, pressure and temperature measurements alone will not be enough to determine the enthalpy. However if an additional measurement of quality is made the enthalpy is then defined. In addition, there may be other applications in refrigeration cycles.

The ability to measure the flow rate and composition of the saturated vapor/liquid mixtures within the conduits is an important aspect of any system or strategy design to optimize the performance of a system based on saturated vapor/liquid mixtures. The industry recognizes this, and has been developing a wide variety of technologies to perform this measurement. These include probe based devices, sampling devices, venturis and ultrasonic devices This invention provides an apparatus and method to measure homogeneous and/or non-homogeneous fluids used in industrial systems having various working fluids to determine various parameters of the process fluid, such as the volumetric flow of the fluid, the consistency or composition of the fluid, the density of the fluid, the Mach number of the fluid, the size of particle flowing through the fluid, the air/mass ratio of the fluid and/or the percentage of entrained air within a liquid or slurry.

Here a novel approach to flow measurements is proposed which utilizes a non-intrusive, externally mounted sensing element that requires no moving parts and is highly reliable. This approach is based upon signal correlation of unsteady pressure measurements induced in an array of externally mounted sensors. For a saturated vapor/liquid fluid mixture, the apparatus of the present invention can measure the vapor quality of the fluid mixture.

SUMMARY OF THE INVENTION

Objects of the present invention include an apparatus for measuring the unsteady pressures of a homogeneous or non-homogeneous fluid flow within a large diameter pipe to determine a parameter of the fluid.

According to the present invention, an apparatus for measuring at least one parameter of a fluid flowing within a pipe includes a spatial array of at least two sensors, disposed at different axial locations along the pipe. Each sensor measures a parameter within the pipe at a corresponding axial location. Each of the sensors provides a signal indicative of a parameter within the pipe at said axial location of a corresponding one of said sensors. Each sensor includes at least two sensing elements disposed circumferentially at the corresponding axial location. A signal processor, responsive to said signals, provides a signal indicative of the at least one parameter of the fluid in the pipe.

According to the present invention, an apparatus for determining internal pressure changes of a medium flowing in a pipe is provided. At least one sensor is coupling to an outer surface of the pipe by a coupling arrangement, responsive to radial expansion and contraction of the pipe caused by internal pressure changes of a medium flowing therein, for providing a sensor signal containing information about the radial expansion and contraction of the pipe. A processor module, responsive to the sensor signal, provides a processor module signal containing information about the internal pressure changes of the medium flowing in the pipe.

The foregoing and other objects, features and advantages of the present invention will become more apparent in light of the following detailed description of exemplary embodiments thereof.

BEST MODE FOR CARRYING OUT THE INVENTION

Figure 1:
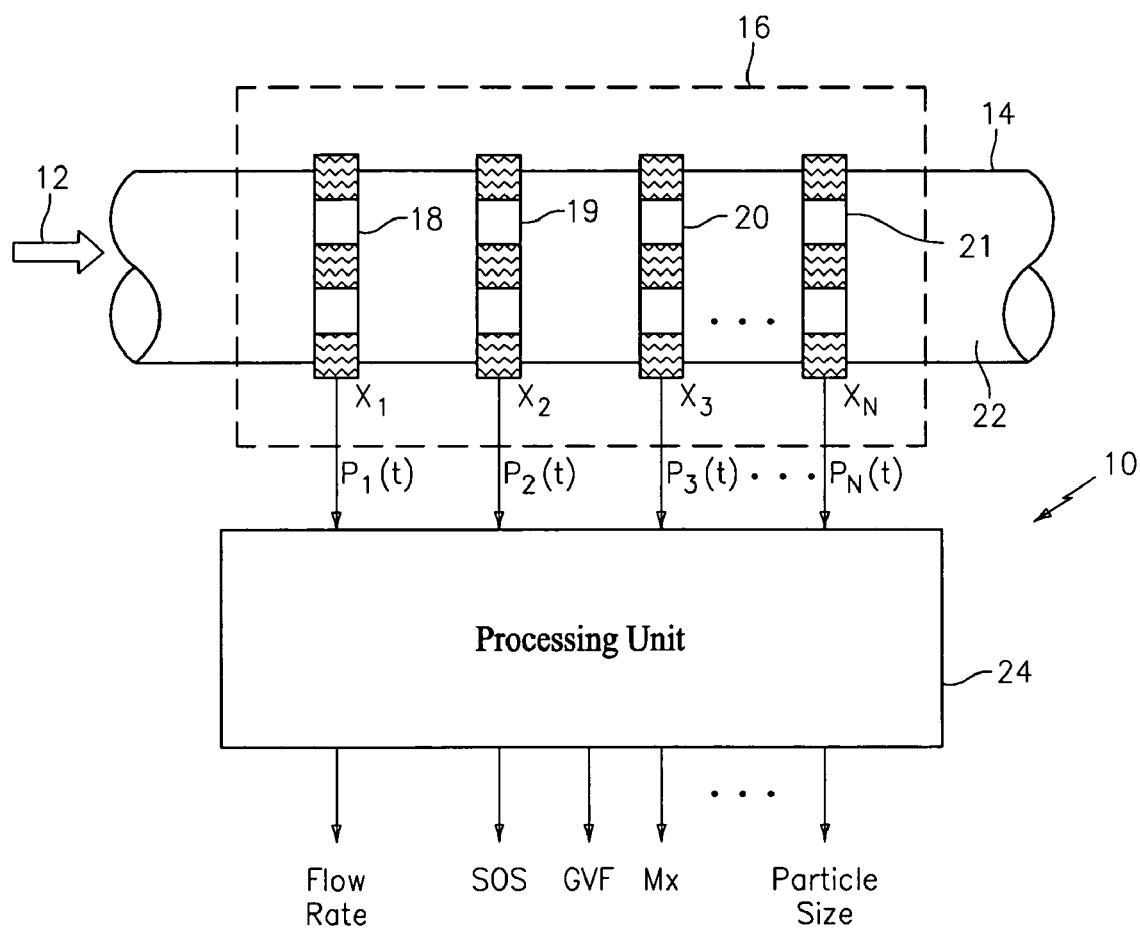
FIG. 1 is a schematic illustration of an apparatus having an array of segmented sensors disposed along a pipe for measuring a parameter of a fluid flowing in the pipe, in accordance with the present invention.

Referring to FIG. 1, an apparatus or flow meter, generally shown as 10, is provided to measure the unsteady pressures (P(t)) of a homogeneous or non-homogeneous fluid 12 flowing within a pipe or conduit 14 to determine a parameter or characteristic of the fluid. The apparatus described herein after is particularly advantageous for measuring certain characteristics of fluid flowing through large diameter pipes, which is greater than six inches in diameter. The apparatus is scalable to any large diameter pipe greater than six inches. In fact, one embodiment of the present invention has been demonstrated on a pipe having an outer diameter of at least 55 inches.

The flow meter 10 can measure the velocity and/or volumetric flow rate of a single phase fluid 12 (e.g., gas, liquid or liquid/liquid mixture) and/or a multi-phase mixture 12 (e.g., process flow) flowing through a pipe. The multi-phase mixture may be a two-phase liquid/gas mixture, a solid/gas mixture or a solid/liquid mixture, gas entrained liquid or a three-phase mixture.

As will be described in greater detail hereinafter with respect to one embodiment of the present invention, the apparatus may be clamped onto a large diameter pipe. This clamp-on embodiment permits ease of installation and allows the apparatus to be installed, maintained, serviced and removed without having to interruption of the process flow. One will appreciate that the larger the diameter of the pipe, the more advantageous the present invention is compared with other flow meters currently on the market, such as magmeters and coriolis meters. Further, the clamp on meter does not interrupt the fluid flow and thus cause pressure drops in the pipe. Other types of meter having elements within the pipe (e.g., vortex meter) obstruct the flow and reduces the energy in the flow that increases costs of pumping the fluid.

The apparatus 10 includes a sensing device 16 that comprises an array of pressure sensors 18–21 axially spaced along the outer surface 22 of the pipe 14. The measurements of the unsteady pressures are provided to a processing unit 24, which processes the pressure measurements ($P_1(t)$–$P_N(t)$) and determines at least one parameter of the fluid. Specifically, the characteristics and parameters determined may include the volumetric flow of the fluid, the consistency or composition of the fluid, the density of the fluid, the Mach number of the fluid, the size of particle flowing through the fluid, the air/mass ratio of the fluid, the mass flow and/or the percentage of entrained air within a liquid or slurry.

In an embodiment of the present invention shown in FIG. 1, the apparatus has four pressure sensors 18–21 disposed axially along the pipe for measuring the unsteady pressure of the fluid flowing therethrough. While the flow meter embodying the present invention comprising a meter having at least four (4) pressure sensors 18–21, the invention contemplates having at least 2 pressure sensors to as many 16 pressures. The apparatus 10 has the ability to measure the volumetric flow rate and other fluid parameters using one or both of the following techniques described herein below:

1) Determining the velocity of unsteady pressure variations by sensing the vortical disturbances of the fluid using the array of pressure transducers 18–21, and/or
2) Determining the speed of sound of acoustical disturbances or sound waves propagating through the fluid using the array of pressure transducers 18–21.

Generally, the first technique measures the velocities associated with unsteady flow fields and/or pressure disturbances (e.g., vortical disturbances). The pressure sensors measure the unsteady pressures created by the vortical disturbances as these disturbances convect within the fluid in a known manner with reference to the fluid in the pipe. Therefore, the velocity of these vortical disturbances is related to the velocity of the fluid and hence the volumetric flow rate may be determined, as will be described in greater detail hereinafter.

Alternatively, the second technique measures unsteady pressures created by acoustical disturbances propagating through the fluid to determine the speed of sound (SOS) of the acoustical disturbances. Knowing the pressure and/or temperature of the fluid and the speed of sound of the acoustical disturbances, the processing unit can determine the mass flow rate, the consistency of the fluid (i.e., the mass/air ratio, the mass/liquid ration, the liquid/air ratio), the density of the fluid, the enthalpy of the fluid, and the Mach number of the fluid, and the size of particles with the fluid, which will be described in greater detail hereinafter.

In one embodiment of the present invention as shown in FIG. 1, each of the pressure sensors 18–21 may include a plurality of piezoelectric sensor or piezoelectric film sensor 23 to measure the unsteady pressures of the fluid 12 using either technique described hereinbefore.

The piezoelectric film sensors 23 include a piezoelectric material or film 25 to generate an electrical signal proportional to the degree that the material is mechanically deformed or stressed. The piezoelectric film 25 can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor 23 that may be used for the present invention is part number 1-1002405-0, LDT4-028K, manufactured by Measurement Specialties, Inc.

Piezoelectric film 25, like piezoelectric material, is a dynamic material that develops an electrical charge proportional to a change in mechanical stress. Consequently, the piezoelectric material measures the strain induced within the process pipe 14 due to unsteady pressure variations (e.g., vortical and/or acoustical) within the process fluid 12. Strain within the conduit is transduced to an output voltage or current by the attached piezoelectric sensor. The piezoelectrical material or film may be formed of a polymer, such as polarized fluoropolymer, polyvinylidene fluoride (PVDF).

Figure 2:
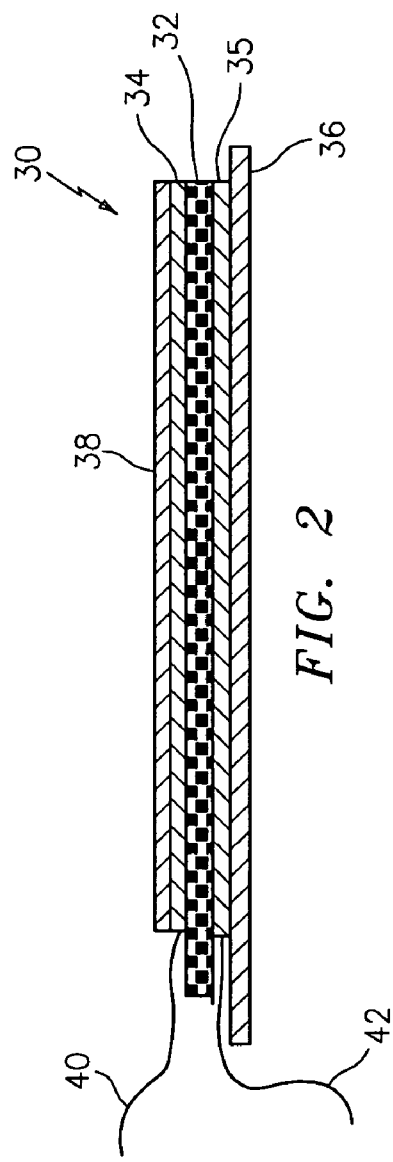
FIG. 2 is a cross-sectional view of a piezoelectric film sensor, in accordance with the present invention.
Figure 3:
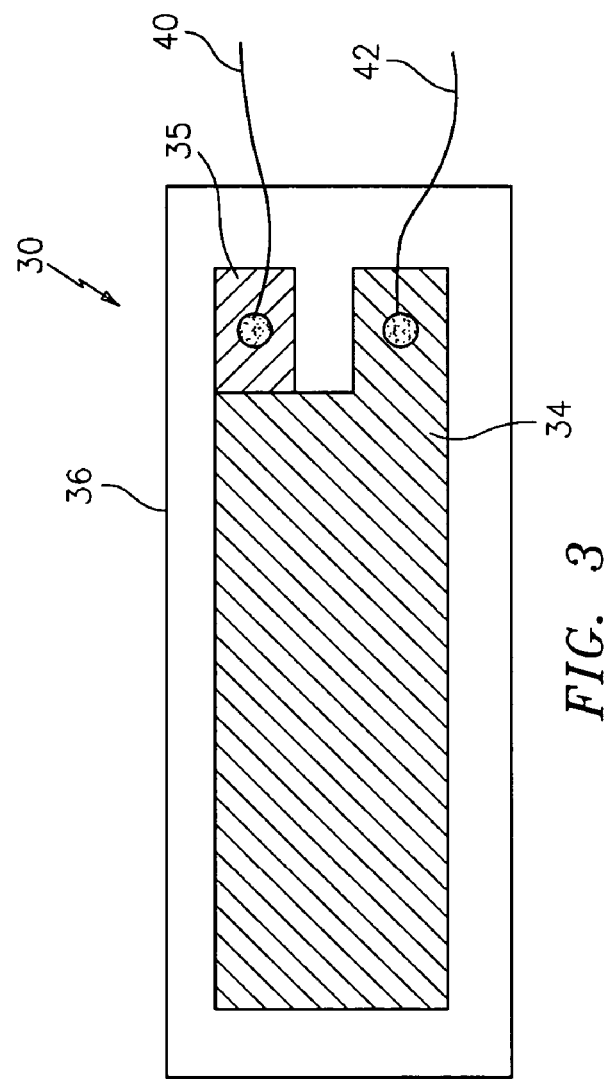
FIG. 3 is a top plan view of the piezoelectric film sensor of FIG. 2.

FIGS. 2 and 3 illustrate a piezoelectric film sensor, similar to the sensor 18 of FIG. 1, wherein the piezoelectric film 32 is disposed between and pair of conductive coatings 34,35, such as silver ink. The piezoelectric film 32 and conductive coatings 34,35 are coated onto a protective sheet 36 (e.g., mylar) with a protective coating 38 disposed on the opposing side of the upper conductive coating. A pair of conductors 40,42 is attached to a respective conductive coating 34,35.

The thickness of the piezoelectric film 32 may be in the range of 20 um to approximately 100 um. The thickness of the dependent on the degree of sensitivity desired or needed to measure the unsteady pressures within the conduit 14. The sensitivity of the sensor 30 increases as the thickness of the piezoelectric film increases.

Figure 4:
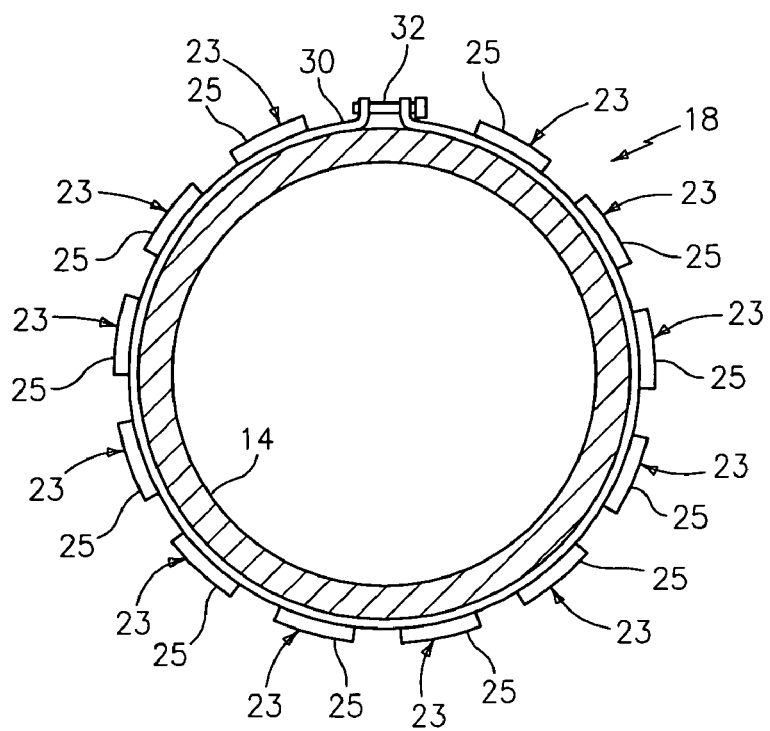
FIGS. 4–7 is a side elevational view of a pressure sensor having a plurality of film sensors mount to a strap that is clamped around the outer surface of a pipe, in accordance with the present invention.
Figure 9:
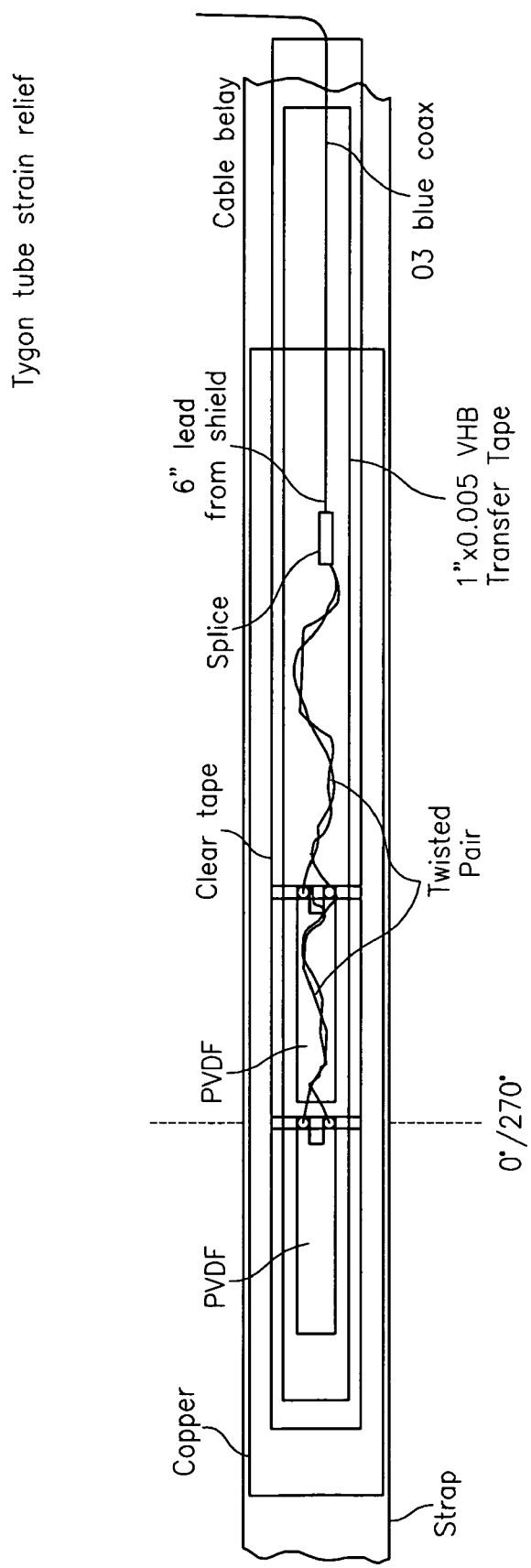
FIG. 9 is a top plan view of a portion of a pressure sensor embodying the present invention.

As shown in FIGS. 4, a plurality of film sensors are disposed circumferentially spaced around the outer surface of the pipe 14. The film sensors 23 provide a circumferentially average of the pressure at each of the locations $x_1$–$x_N$ to be provided to the processor 24. As will be described in greater detail hereinafter, the film sensors 23 are mounted to a metallic (e.g., stainless steel) strap 30, which is clamped onto the outer surface the pipe by a bolt 32. The circumferentially spaced film sensors are connected in parallel. As shown in FIG. 9, the twisted leads of one film sensor may be directly connected to the terminals or rivets of the adjacent film sensor. Alternatively, the twisted leads of each film sensor 23 may be directly connected to the processor. Advantages to having a pressure sensors formed of circumferentially spaced film sensors include reduced cost by reducing the amount of film sensing material necessary to provide a circumferentially average measurement of the pipe which can be significant for the much larger diameter pipes. Further, the film sensors provide robustness because the apparatus will still function if a film sensor fails, thereby providing redundancy. Also, the plurality of film sensors per pressure sensor allows portions of the pressure sensor to be selectable. For example, the processing unit 24 may selectively read the film sensor of each pressure sensor.

Figure 5:
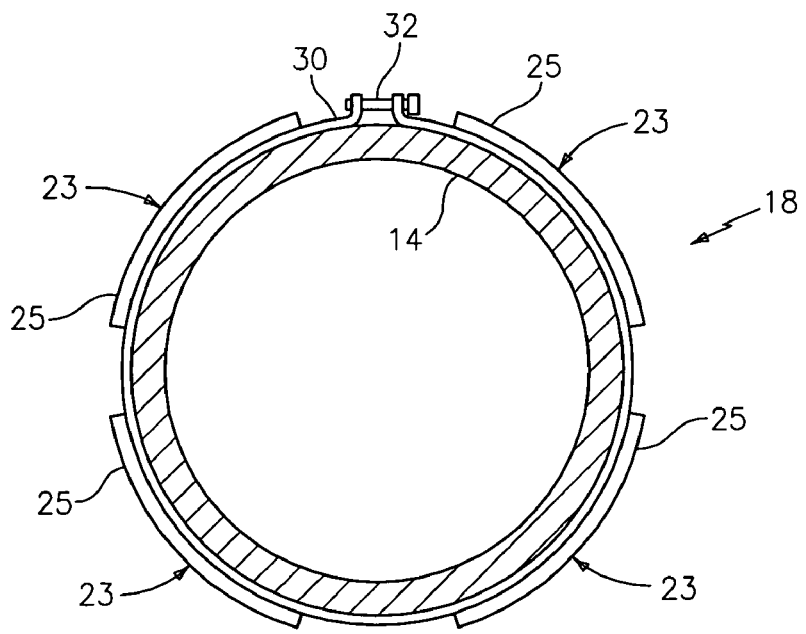
Figure 6:
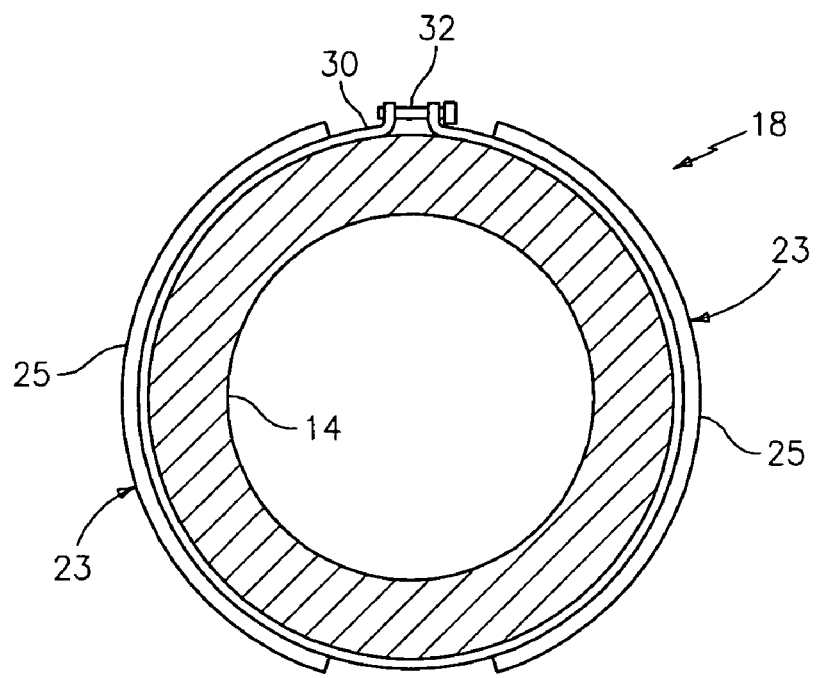
Figure 7:
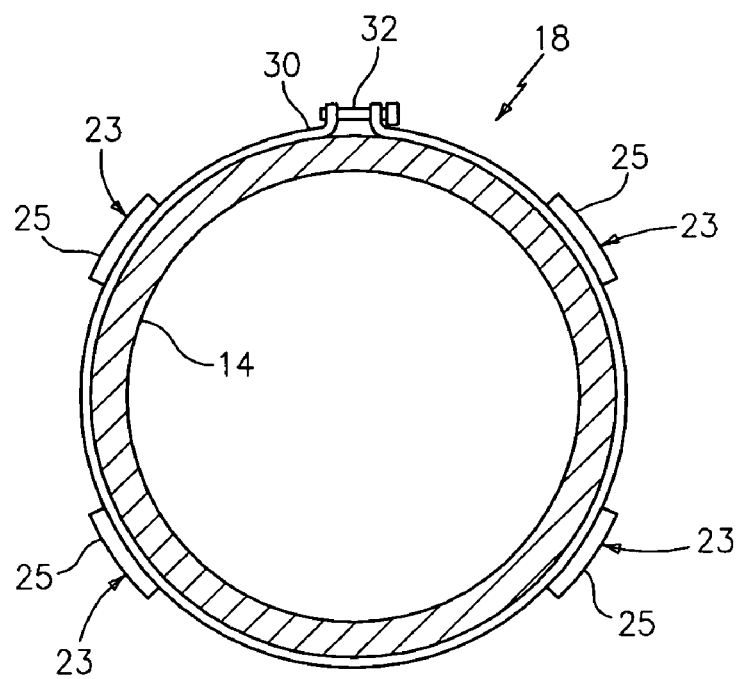

The present invention contemplates any number of film sensors disposed about circumference of the pipe at each location, spaced at any predetermined distance. The film sensor may be equi-spaced or not. The length of each film sensor may be any desirable length to measure a desirable circumferential length of the pipe. Other examples of a pressure sensor 18–21 embodying the present invention is shown in FIGS. 5–7. In FIG. 5 a pressure sensor 18 comprises four piezoelectric film sensors 23 disposed about the circumference of the pipe. Each film sensor measures the pressure of a substantial portion of one quarter of the circumference of the pipe. Referring to FIG. 6, a pressure sensor 18 comprises a pair of film sensors 23 disposed about the circumference of the pipe 14. Each film sensor measures the pressure of a substantial portion of one half of the circumference of the pipe. FIG. 7 shows another embodiment of a pressure sensor 18 having four piezoelectric film sensors 23 substantially equally spaced about the circumference of the pipe, similar to that shown in FIG. 5 however the film sensor 23 measures the pressure of a shorter circumferential length.

The type of unsteady pressure measurement being made determines the spacing of the pressure sensors 18–21. The characteristics of the unsteady vortical pressures dictate the length of the array, and therefore the spacing of the pressure sensors 18–21, to be less than the coherence length of the vortical disturbances which is typically on the order of a pipe diameter. Correlation of unsteady vortical pressure measurements between sensors is used to determine the bulk flow rate of the process fluid, which will be described in greater detail hereinafter.

Mass flow rates and other parameters, described hereinbefore, are determined by measuring the speed of sound within the process fluid 12. These parameters are determined by correlating unsteady pressure variations created by acoustic disturbances within the process fluid. In this case, the wavelength of the measured acoustic signal determines the sensor spacing. The desired wavelength of the measured acoustic signal is dependent upon the dispersion of particles in the fluid flow, which is dependent on the particle size, which will be described in greater detail hereinafter, which is similar to that describe in U.S. patent application Ser. No. 10/349,716, filed Jan. 23, 2003 and U.S. patent application Ser. No. 10/376,427, filed Feb. 26, 2003, which are incorporated herein by reference.

The clamp-on technique provides low cost, non-intrusive flow measurements that requires no excitation source. Ambient flow noise is used as a source. Further, flexible piezoelectric sensors 23 can be mounted in a variety of configurations to enhance signal detection schemes, that include co-located sensors, segmented sensors with opposing polarity configurations, wide sensors to enhance acoustic signal detection and minimize vortical noise detection, tailored sensor geometries to minimize sensitivity to pipe modes, and differencing of sensors to eliminate acoustic noise from vortical signals. The film sensors 23 operate at relatively high temperatures (140C) (e.g., co-polymers).

Figure 30:
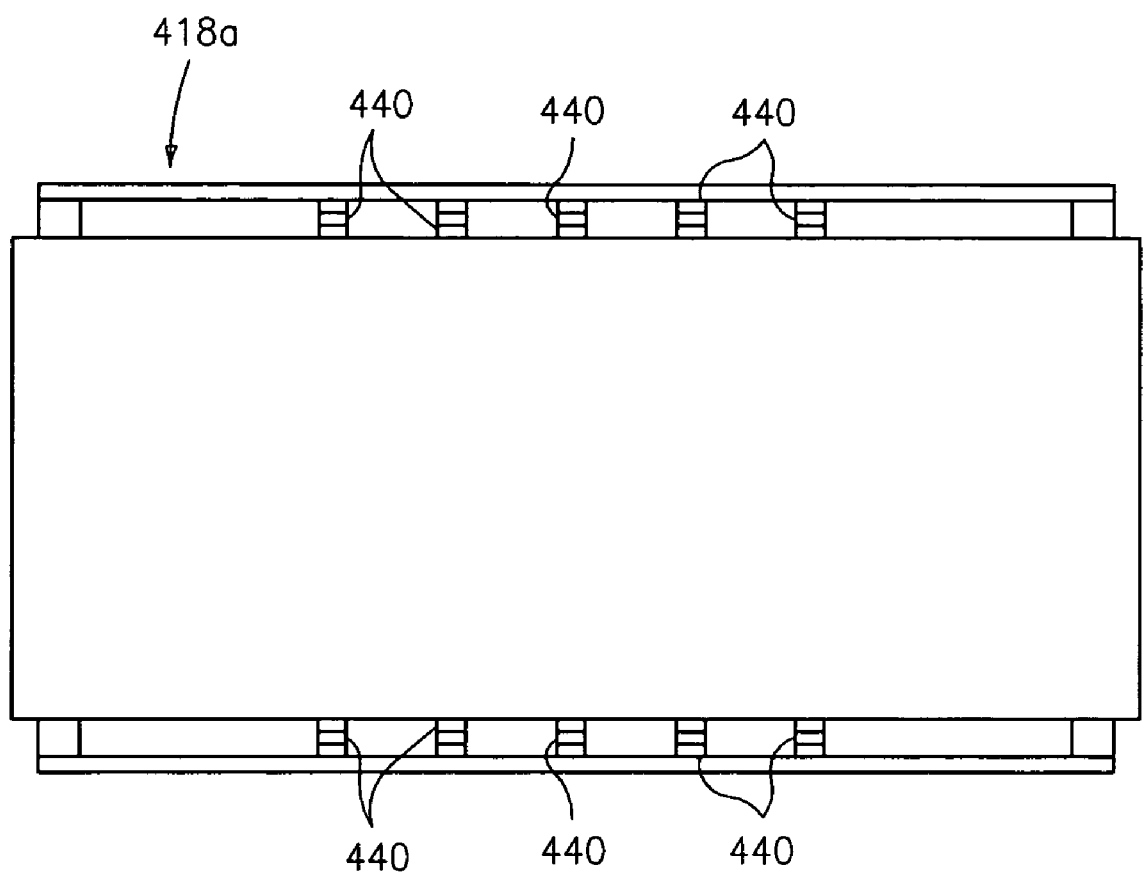
FIG. 30 shows an embodiment of the invention wherein the pipe is encased in a shell having sensor therein in accordance with the present invention.

As suggested hereinbefore, a clamp-on flow meter 10' embodying the present invention, as shown in FIG. 30, was installed on a large diameter pipe 14' to measure the volumetric flow of the fluid flowing therein. The method of determining the volumetric flow of the fluid will be described in greater detail hereinafter. The pipe 14' had an outer diameter of approximately 55 inches. The sensing portion or measurement region 16' of the flow meter 10' includes four pressure sensors 18',19',20',21', similar to the sensing portion 16 shown and described hereinbefore. The clamp-on sensors 18'–21' was equally spaced along the axis of the pipe 14. The length of the array of pressure sensors was approximately 12 inches apart or approximately 20% of the diameter of the pipe 14.

Figure 8:
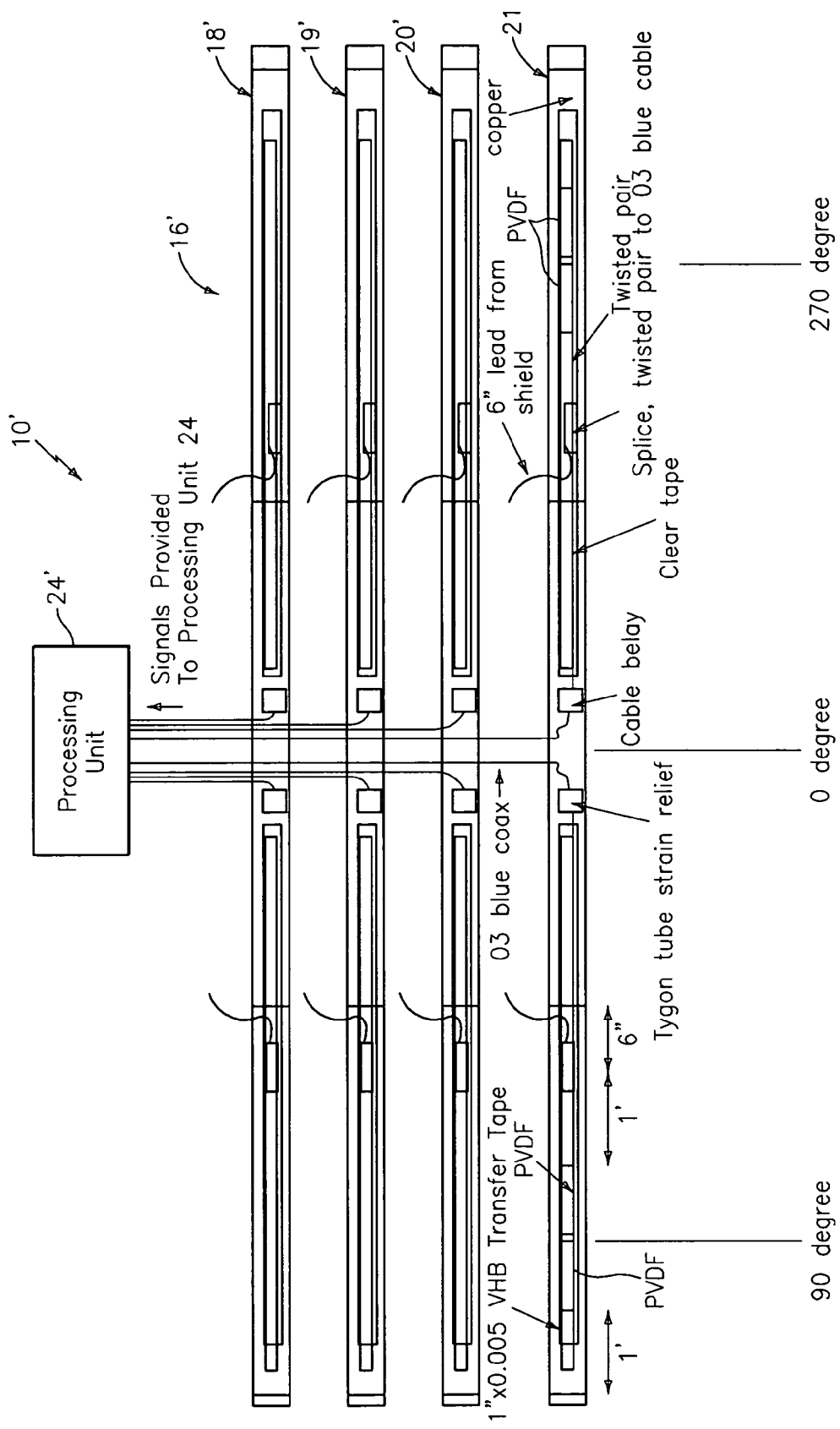
FIG. 8 is a top plan view of a disassembled array of pressure sensors and processing unit, in accordance with the present invention.
Figure 10:
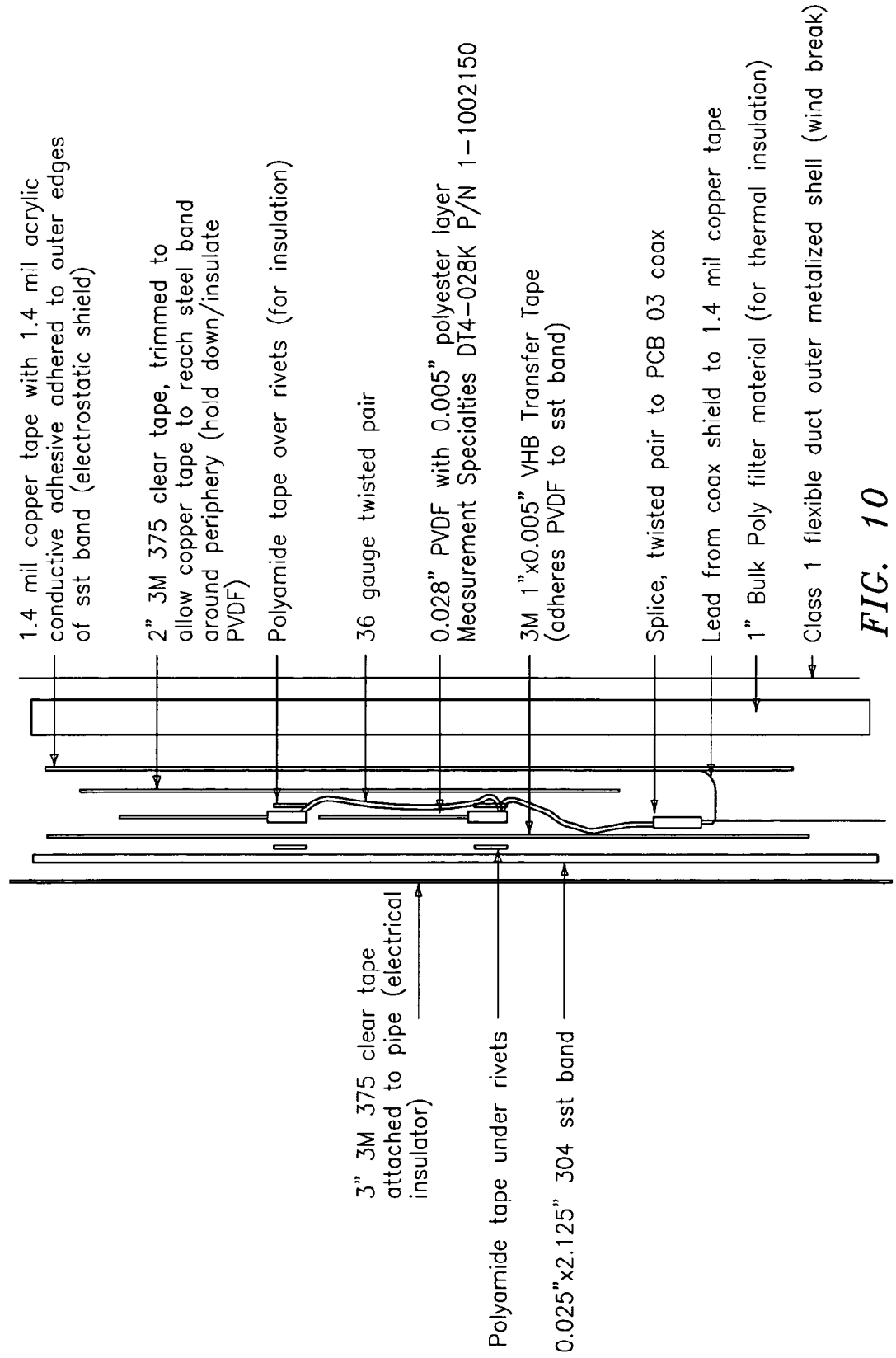
FIG. 10 is an exploded side view of a portion of the pressure sensor embodying the present invention.

Referring to FIGS. 8–10, each of the pressure sensors 18'–21' includes two pairs of piezoelectric film (PVDF) sensors 23' mounted on a respective stainless steel strap 30', wherein each pair of PVDF sensors are mounted approximately 180 degrees apart. Each strap was wrapped around the pipe and the free ends of the straps are clamped together by a plurality of bolts or other fasteners, similar to that described hereinbefore. Each of the PVDF sensors 23' is approximately 6 inches in length.

FIG. 8 illustrates an expanded top plane view of a section of a pressure sensor 18', for example. FIG. 10 illustrates an exploded side elevational view of the pressure sensor 18' of FIG. 9. As shown in FIGS. 9 and 10, a clear tape is adhered to the outer surface of the pipe to provide an electrical insulator between the pipe and the pressure sensor 18'. Each pressure sensor 18'–21' includes a strap formed of 300 series stainless steel, approximately 2.125" wide and 0.025 inches thick. The PVDF sensors and splice are attached to the strap by a transfer tape. A pair of twisted wires is attached to rivets electrically attached to the poles of the pair PVDF sensors to connect the PVDF in parallel. A pair of twisted wires provides the output signal of the PVDF sensors to a coaxial cable, which then provides the signal to the processing unit 24'. Polyimide tape is also disposed on top of and below the rivets of each of the PVDF sensors. Copper tape having a conductive adhesive is then adhered to the top PVDF sensors by clear tape such that the copper tape can be adhered to the outer edges of the strap to provide an electrical ground shield.

Each of these sensors 18'–21' are then mounted to the flow pipe. A one inch blanket of poly filter material is wrapped around the four sensors to provide thermal insulation. A flexible duct having a metalized shell is wrapped around the insulative material to provide a wide break.

Figure 11:
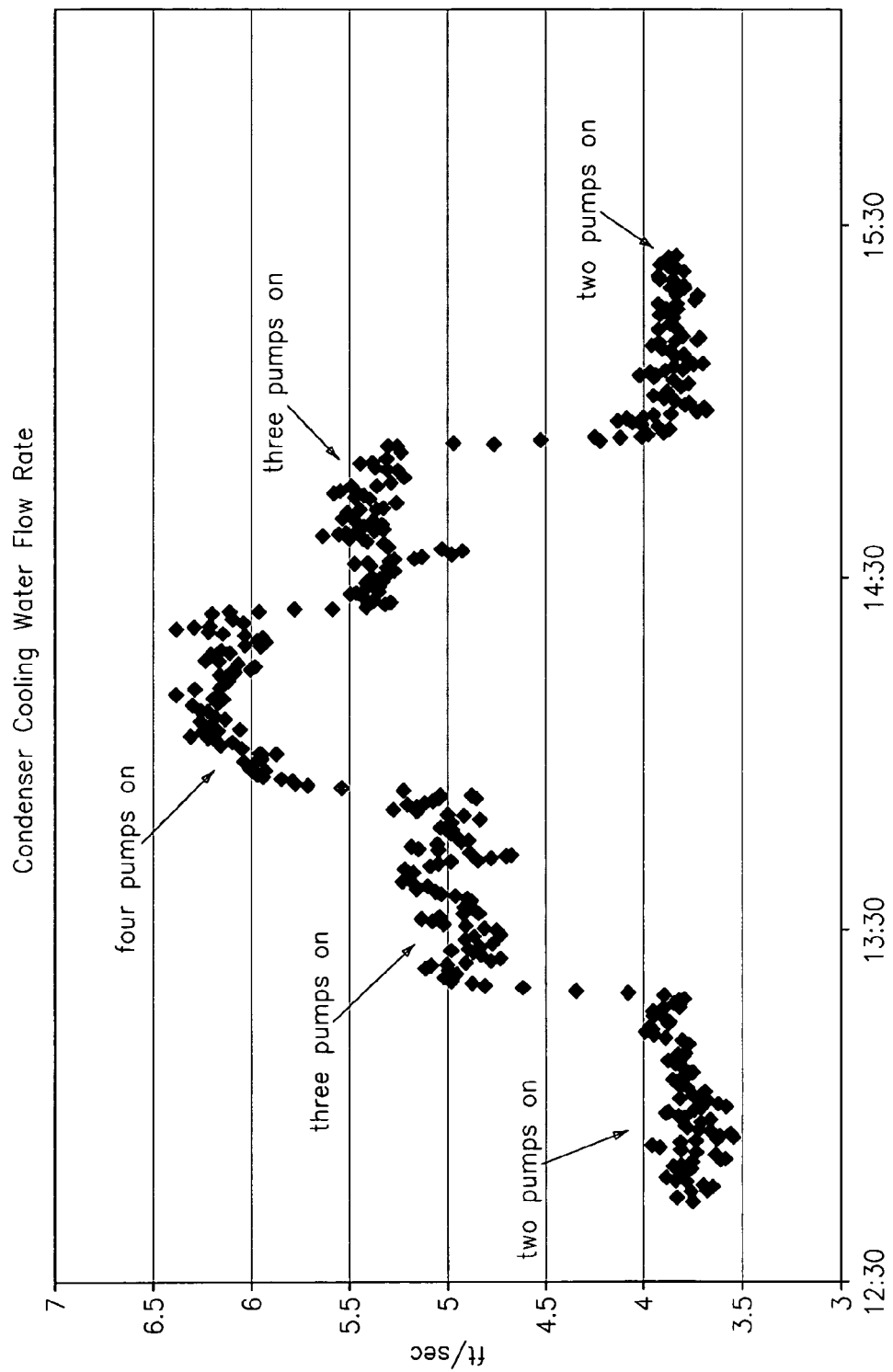
FIG. 11 is a data of the flow rate of a condenser cooling water using a flow meter embodying the present invention.

FIG. 11 is a plot of data recorded with the large diameter flow meter 10' that measured the flow rate of condenser cooling water flowing through a pipe having an outer diameter of approximately 55 inches. The data shows the flow rate measured by the meter 10' as a function of time (over a 3 hour period). The plot illustrates the change in flow rate of the water within the pipe changing as additional pumps come on line to draw additional water through the pipe. The initial measurement or plateau shows the flow rate when 2 pumps are operating. The second measurement shows the flow rate when 3 pumps are operating. The third measurement shows the flow rate when 4 pumps are operating and so forth.

Figure 12:
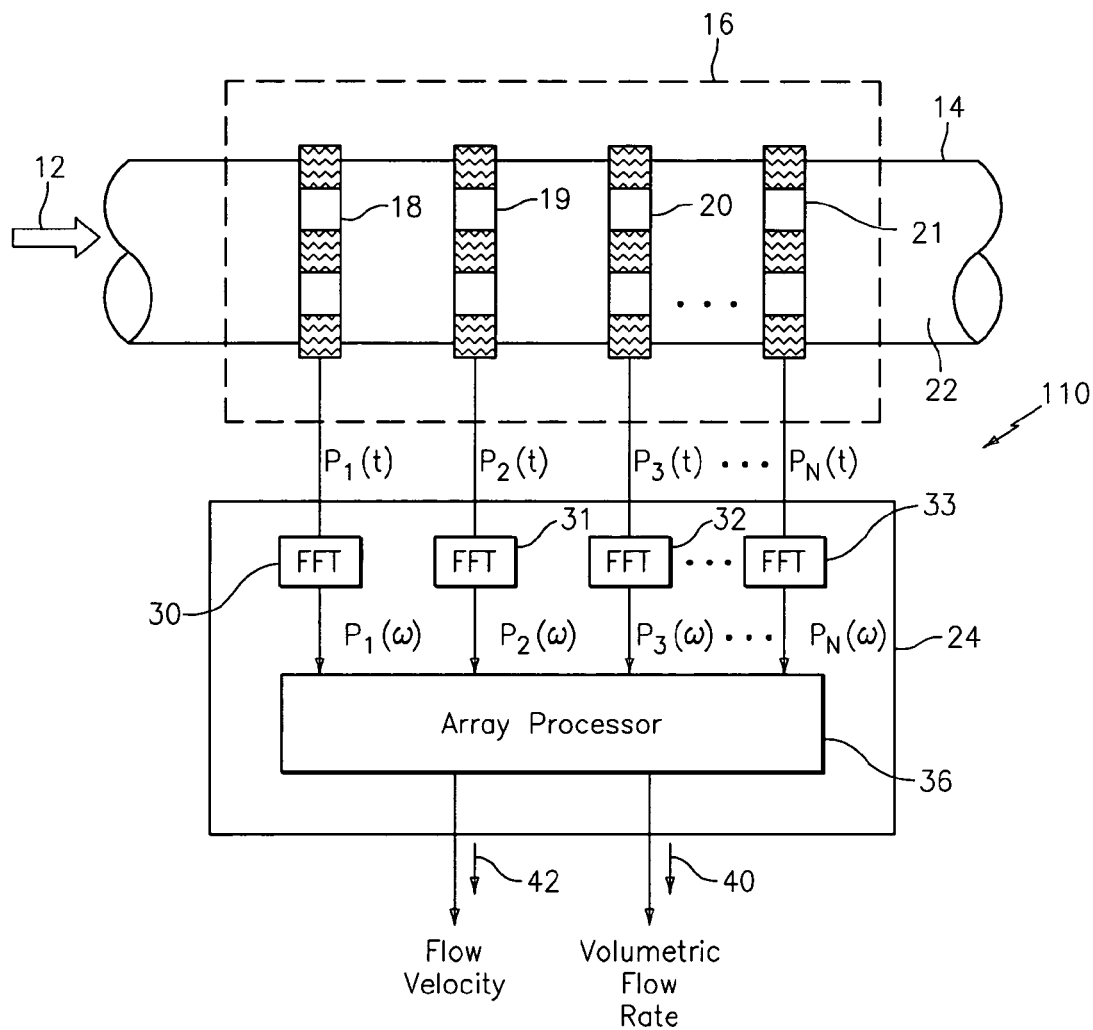
FIG. 12 is a schematic illustration of a meter for measuring the vortical fields having an array of segmented sensors disposed along a pipe for measuring a parameter of a fluid flowing in the pipe, in accordance with the present invention.

In one example, the flow meter 110 of FIG. 12 measures the volumetric flow rate by determining the velocity of vortical disturbances or "eddies" 45 (see FIG. 12) propagating with the flow 12 using the array of pressure sensors 18–21. The flow meter 10 measures the velocities associated with unsteady flow fields created by vortical disturbances or "eddies" 45 and other inhomogenities to determine the velocity of the flow 12. The pressure sensors 18–21 measure the pressure $P_1(t)$–$P_N(t)$ of the respective pressure signals at each axial location of the pressure sensors, which vary due to the vortical disturbances as these disturbances convect within the flow 12 through the pipe 14 in a known manner. Therefore, the velocity of these vortical disturbances is related to the velocity of the flow 12 and hence the volumetric flow rate may be determined, as will be described in greater detail hereinafter. The volumetric flow is determined by multiplying the velocity of the fluid by the cross-sectional area of the pipe 14.

To measure volumetric flow, the flow meter 10 characterizes the velocity at which coherent vortical structures convect past the axial array of sensor units 18–21. Coherent structures 45 are an inherent feature of turbulent boundary layers present in all turbulent flows. Unlike conventional vortex shedding meters, no internal geometry is required to generate these structures.

While the array processor 36 processes each of the input signals $P_1(t)$–$P_N(t)$, the present invention contemplates differencing adjacent pairs of pressure sensors 18–21 and provides the differenced signal to the array processor to filter out the acoustic pressures.

The overwhelming majority of industrial process flows 12 involve turbulent flow. Turbulent fluctuations within the process flow govern many of the flow properties of practical interest including the pressure drop, heat transfer, and mixing. For engineering applications, considering only the time-averaged properties of turbulent flows is often sufficient for design purposes. For sonar based array processing flow metering technology, understanding the time-averaged velocity profile in turbulent flow 12 provides a means to interpret the relationship between speed at which coherent structures 45 convect and the volumetrically averaged flow rate.

Figure 13:
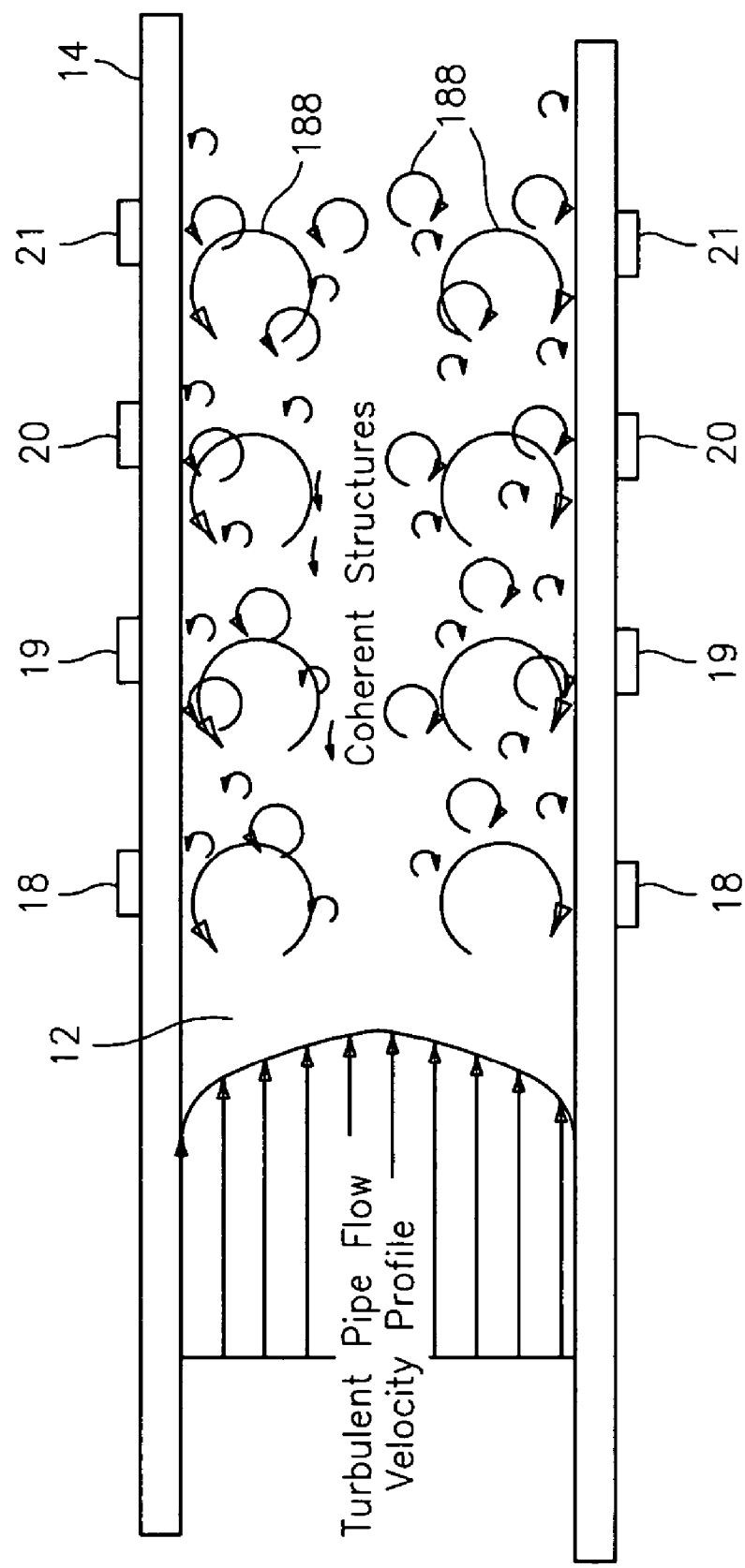
FIG. 13 is a cross-sectional view of a pipe having a turbulent pipe flowing having coherent structures therein, in accordance with the present invention.

FIG. 13 illustrates the relevant flow features of turbulent pipe flow 12 along with an axial array of at least two pressure sensors 18–21. As shown, the time-averaged axial velocity is a function of radial position, from zero at the wall to a maximum at the centerline of the pipe. The flow 12 near the wall is characterized by steep velocity gradients and transitions to relatively uniform core flow near the center of the pipe 14. Vortical structures, often termed turbulent eddies, are superimposed over time averaged velocity profile. These coherent structures contain temporally and spatially random fluctuations with magnitudes typically less than 10% percent of the mean flow velocity and are carried along with the mean flow. Experimental investigations have established that eddies generated within turbulent boundary layers remain coherent for several pipe diameters and convect at roughly 80% of maximum flow velocity (Schlichting, 1979).

The Reynolds number (Re), based on pipe diameter (D), characterizes many of the engineering properties of the flow. The Reynolds number is a non-dimensional ratio representing the relative importance of inertial forces to viscous forces within a flow:

$$Re = \frac{\text{inertial}}{\text{viscous}} \text{forces} = \frac{\rho u \frac{\partial u}{\partial x}}{\mu \frac{\partial^2 u}{\partial y^2}} = \frac{UD}{v}$$

Where $\rho$ is the fluid density, $\mu$ is the dynamic viscosity, U is the volumetrically averaged flow velocity and $\upsilon$ ($=\mu/\rho$) is the kinematic viscosity.

The critical Reynolds number for pipe flows, above which flows are considered turbulent, is ~2300. In addition to demarcating a boundary between laminar and turbulent flow regimes, the Reynolds number is a similarity parameter for pipe flows, i.e. flows in geometrically dissimilar pipes with the same Reynolds number are dynamically similar (Schlichting p.12).

As shown in FIG. 12, the flow meter 110 embodying the present invention has an array of at least two pressure sensors 18–19, located at locations $x_1,x_2$ axially along the pipe 14. One will appreciate that the sensor array may include three or more pressure sensors as depicted by pressure sensors 20, 21 at locations $x_3$, $x_N$, respectively. The present invention contemplates that the array 16 may comprise any number of pressure 18–21 or greater, which includes arrays that may have between 2 and 16 pressure sensors. The pressure sensors provide transit time-varying signals $P_1(t),P_2(t),P_3(t),P_N(t)$ to a signal processor 24 to known Fast Fourier Transform (FFT) logics 30–33, respectively. The FFT logics 30–33 calculate the Fourier transform of the time-based input signals $P_1(t)$–$P_N(t)$ and provide complex frequency domain (or frequency based) signals $P_1(\omega),P_2(\omega),P_3(\omega),P_N(\omega)$ indicative of the frequency content of the input signals. Instead of FFT's, any other technique for obtaining the frequency domain characteristics of the signals $P_1(t)$–$P_N(t)$, may be used.

The frequency signals $P_1(\omega)$–$P_N(\omega)$ are fed to an array processor 36, which provides a flow signal 40 indicative of the volumetric flow rate of the process flow 12 and a velocity signal 42 indicative of the velocity of the process flow.

One technique of determining the convection velocity of the vortical disturbances within the process flow 12 is by characterizing the convective ridge of the vortical disturbances using an array of unsteady ultrasonic sensors or other beam forming techniques, similar to that shown in U.S. patent application Ser. No. 09/729,994, filed Dec. 4, 2000, entitled "Method and Apparatus for Determining the Flow Velocity Within a Pipe", now U.S. Pat. No. 6,609,069, which is incorporated herein by reference. This technique of determining the convection velocity of the vortical disturbances will be described in greater detail hereinafter.

The flow metering methodology uses the convection velocity of coherent structure with turbulent pipe flows 12 to determine the volumetric flow rate. The convection velocity of these eddies 45 is determined by applying arraying processing techniques to determine the speed at which the eddies convect past the axial ultrasonic sensor array of distributed along the pipe 14, similar to that used in the radar and sonar fields.

The array processing algorithms determine the speed of the eddies 45 by characterizing both the temporal and spatially frequency characteristics of the flow field. For a series of coherent eddies convecting past a fixed array of pressure sensors 18–21, the temporal and spatial frequency content of pressure fluctuations are related through the following relationship:

$$k = \frac{\omega}{U_{convect}}$$

Here k is the wave number or spatial frequency, defined as $k=2\pi/\lambda$ and has units of 1/length, $\omega$ is the temporal frequency in rad/sec, and $U_{convect}$ is the convection velocity. Thus, the temporal frequency, ω, is linearly related to the spatial frequency, k, by the convection velocity.

In array processing, the spatial/temporal frequency content of time stationary sound fields are often displayed using "k-ω plots". K-ω plots are essentially three-dimensional power spectra in which the power of the field is decomposed into bins corresponding to specific spatial wave numbers and temporal frequencies. On a k-ω plot, the power associated with a pressure field convecting with the flow is distributed in regions, which satisfies the dispersion relationship developed above. This region is termed "the convective ridge" (Beranek, 1992) and the slope of this ridge on a k-ω plot indicates the convective velocity of the pressure field determine by measuring the variation in the pressure by each pressure sensor 18–21. This suggests that the convective velocity of turbulent eddies, and hence flow rate within a pipe, can be determined by constructing a k-ω plot from the output of an array of sensor and identifying the slope of the convective ridge, as will described in greater detail hereinafter.

As described hereinbefore, the apparatus 10 of FIG. 11 is based on the observation that vortical disturbances within a moving fluid (and/or other characteristics of the fluid that convect with the flow, described hereinabove) vary the pressure of the presssure signal, which can be sensed by pressure sensors' 40,42, and that the vortical disturbances move at either the same velocity as the moving fluid, or at a velocity that can be correlated to the velocity of the moving fluid. The array processing can be performed by exploiting what is sometimes called the dispersion relationship associated with convective disturbances (i.e. ω=uk, where ω is the angular frequency of the signal of the vortical disturbance, u is the velocity of the disturbance, and k is the wavenumber of the signal). Convective disturbances in a flowing fluid can be viewed as disturbances that are fixed to the fluid. These disturbances have a spatial variation associated with them. Since the disturbance can be viewed as affixed to the fluid particles, the spatial variations result in temporal variations when sensed by stationary sensors. The spatial wavelength of the disturbances that move with the fluid is thereby linked to the temporal variations observed by the stationary sensors. The present invention relies on utilizing array processing techniques to identify this relationship and thereby determine the convection velocity of the fluid.

The data $P_1(\omega)$–$P_N(\omega)$ accumulated over a sampling interval is provided to the array processor 36, which performs a spatial-temporal (two-dimensional) transform of the sensor data, from the xt domain to the k-ω domain, and then calculates the power in the K-w plane, as represented by k-ω plot.

To calculate the power in the k-ω plane, as represent by a k-ω plot (see FIG. 14) of either the pressure signals or the differenced pressure signals, the array processor 36 determines the wavelength and so the (spatial) wavenumber k, and also the (temporal) frequency and so the angular frequency ω, of various of the spectral components created by the vortical disturbances. There are numerous algorithms available in the public domain to perform the spatial/temporal decomposition of array of pressure sensors 18–21.

Figure 14:
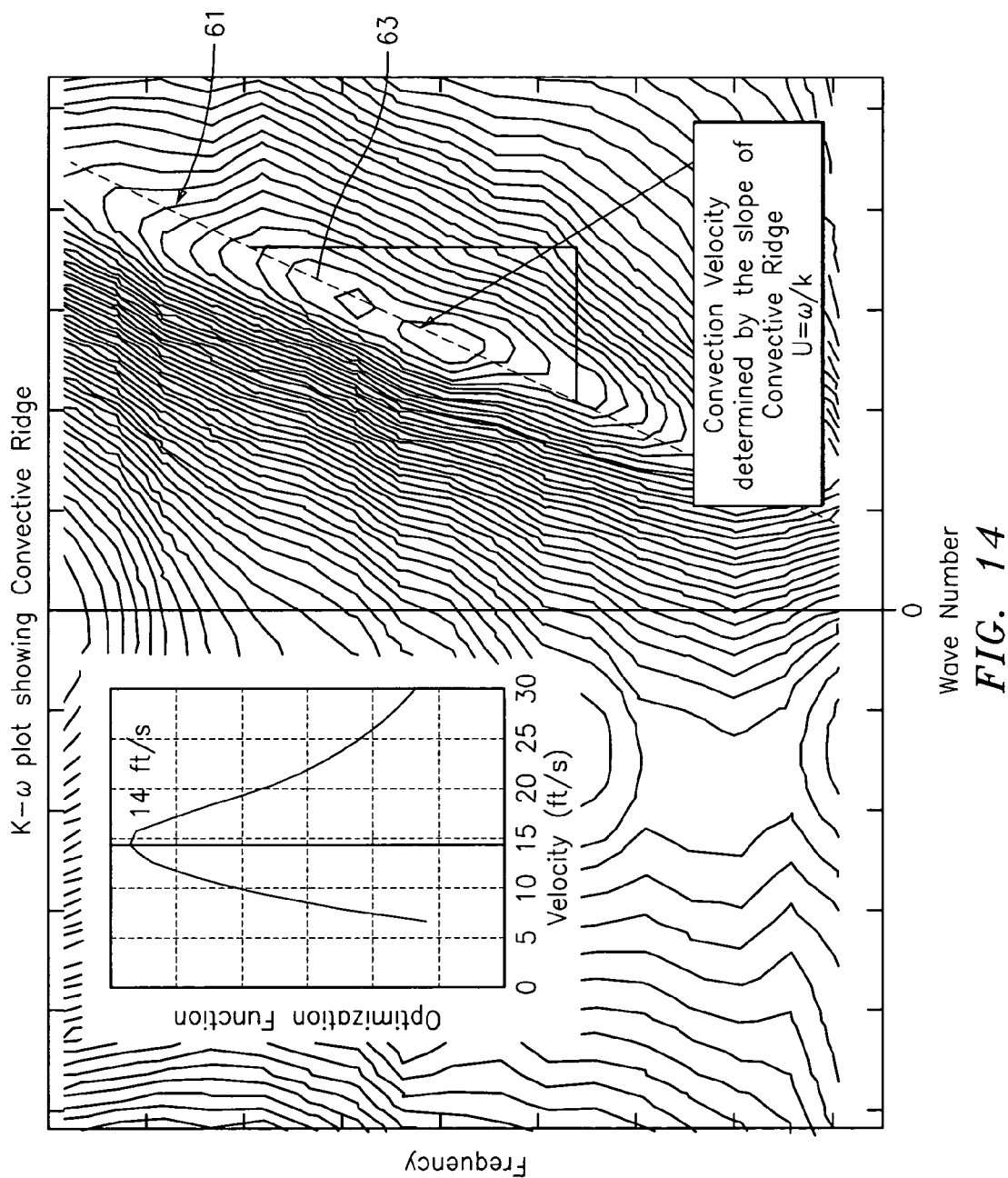
FIG. 14 a kω plot of data processed from an apparatus embodying the present invention that illustrates slope of the convective ridge, and a plot of the optimization function of the convective ridge, in accordance with the present invention.

In the case of suitable vortical disturbances being present, the power in the k-ω plane shown in a k-ω plot of FIG. 14 so determined will exhibit a structure that is called a convective ridge 61. The convective ridge represents the concentration of the disturbances that convect with the flow and is a mathematical manifestation of the relationship between the spatial variations and temporal variations described above. Such a plot will indicate a tendency for k-ω pairs to appear more or less along a line 63 with some slope, the slope indicating the flow velocity, as is described in more detail below. The power in the k-ω plane so determined is then provided to a convective ridge identifier which uses one or another feature extraction method to determine the location and orientation (slope) of any convective ridge present in the k-ω plane. Finally, information including the convective ridge orientation (slope) is used to determine the flow velocity.

The array processor 36 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where λ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by vortical disturbances convecting with a flow are time stationary and have a coherence length long enough that it is practical to locate pressure sensors apart from each other and yet still be within the coherence length.

Figure 15:
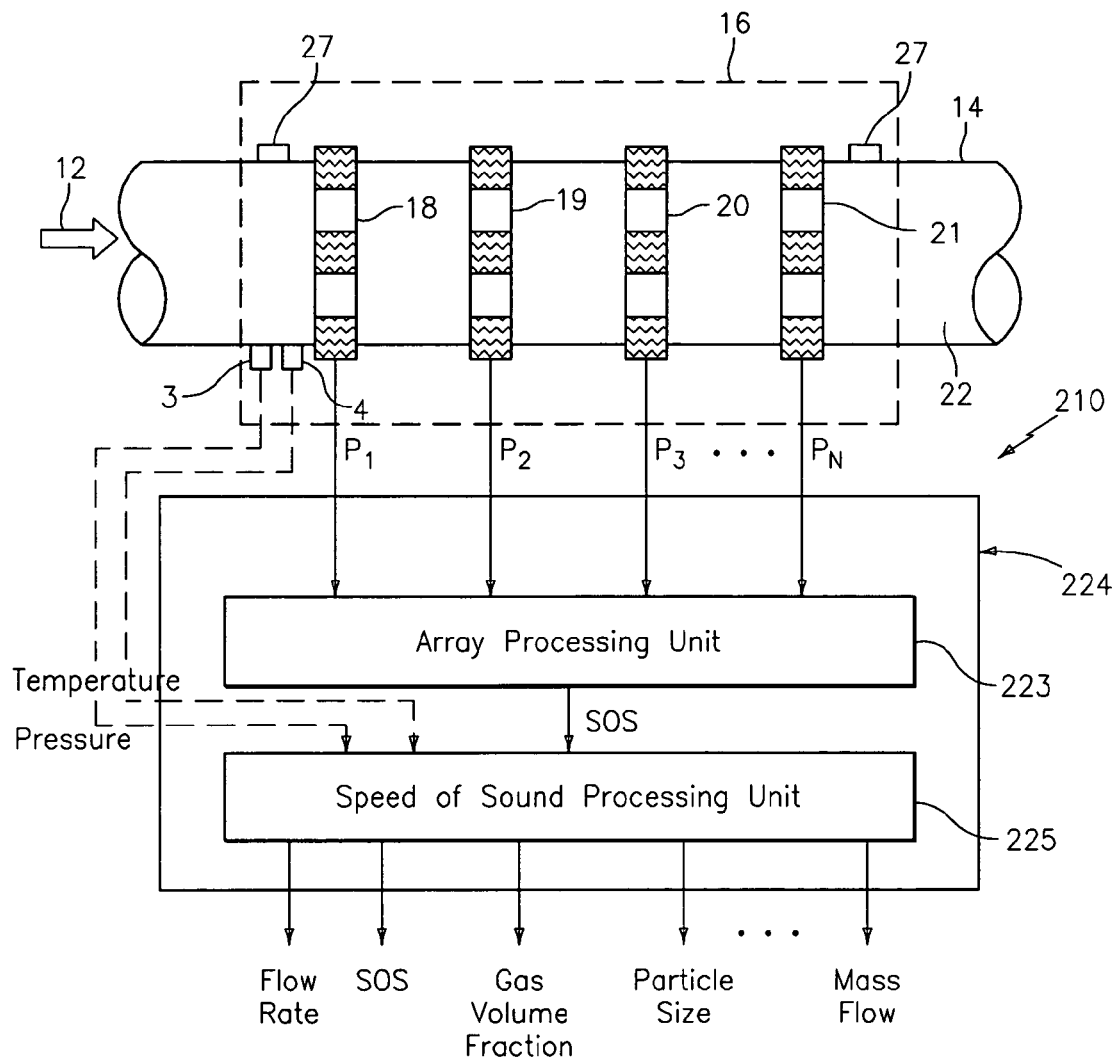
FIG. 15 is a block diagram of an apparatus for measuring the speed of sound propagating through a process flow flowing within a pipe to determine a parameter of the process flow, in accordance with the present invention.

FIG. 15 illustrates a schematic drawing of one embodiment of the present invention. The apparatus 210 includes a sensing device 16 comprising an array of pressure sensors (or transducers) 18–21 spaced axially along the outer surface 22 of a pipe 14, having a process flow propagating therein, similar to that described hereinbefore. The pressure sensors measure the unsteady pressures produced by acoustical disturbances within the pipe, which are indicative of the SOS propagating through the mixture 12. The output signals ($P_1$–$P_N$) of the pressure sensors 18–21 are provided to the processor 224, which processes the pressure measurement data and determines the speed of sound, gas volume fraction (GVF) and other parameters of the flow as described hereinbefore.

In an embodiment of the present invention shown in FIG. 15, the apparatus 210 has at least two pressure sensors 18–21 disposed axially along the pipe 14 for measuring the unsteady pressure $P_1$–$P_N$ of the mixture 12 flowing therethrough. The speed of sound propagating through the flow 12 is derived by interpreting the unsteady pressure field within the process piping 14 using multiple transducers displaced axially over ~2 diameters in length. The flow measurements can be performed using ported pressure transducers or clamp-on, strain-based sensors.

The apparatus 210 has the ability to measure the gas volume fraction and other parameters by determining the speed of sound of acoustical disturbances or sound waves propagating through the flow 12 using the array of pressure sensors 18–21.

Generally, the apparatus 210 measures unsteady pressures created by acoustical disturbances propagating through the flow 12 to determine the speed of sound (SOS) propagating through the flow. Knowing the pressure and/or temperature of the flow and the speed of sound of the acoustical disturbances, the processing unit 224 can determine the gas volume fraction of the mixture, similar to that shown in U.S. patent application Ser. No. 10/349,716, filed Jan. 21, 2003, U.S. patent application Ser. No. 10/376,427, filed Feb. 26, 2003, and U.S. Provisional Patent Application Ser. No. 60/528,802, filed Dec. 11, 2003 which are all incorporated herein by reference.

The apparatus in FIG. 210 also contemplates providing one or more acoustic sources 27 to enable the measurement of the speed of sound propagating through the flow for instances of acoustically quiet flow. The acoustic sources may be disposed at the input end of output end of the array of sensors 18–21, or at both ends as shown. One should appreciate that in most instances the acoustics sources are not necessary and the apparatus passively detects the acoustic ridge provided in the flow 12. The passive noise includes noise generated by pumps, valves, motors, and the turbulent mixture itself.

Figure 16:
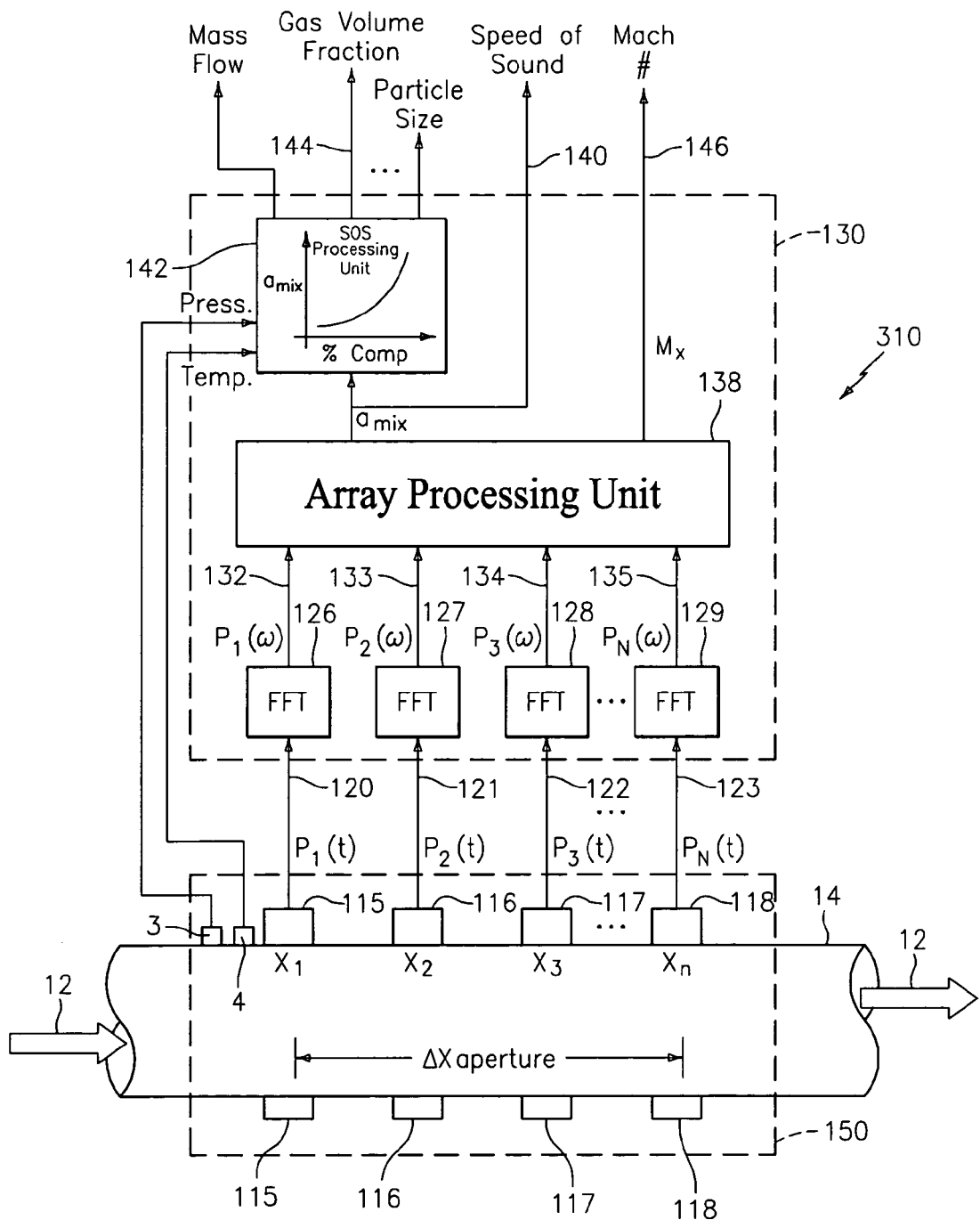
FIG. 16 is a block diagram of another apparatus for measuring the speed of sound propagating through a process flow flowing within a pipe to determine a parameter of the process flow, in accordance with the present invention.

The apparatus 10 of the present invention may be configured and programmed to measure and process the detected unsteady pressures $P_1(t)$–$P_N(t)$ created by acoustic waves propagating through the mixture to determine the SOS through the flow 12 in the pipe 14. One such apparatus 310 is shown in FIG. 16 that measures the speed of sound (SOS) of one-dimensional sound waves propagating through the mixture to determine the gas volume fraction o f the mixture. It is known that sound propagates through various mediums at various speeds in such fields as SONAR and RADAR fields. The speed of sound propagating through the pipe and mixture 12 may be determined using a number of known techniques, such as those set forth in U.S. patent application Ser. No. 09/344,094, entitled "Fluid Parameter Measurement in Pipes Using Acoustic Pressures", filed Jun. 25, 1999, now U.S. Pat. No. 6,354,147; U.S. patent application Ser. No. 09/729,994, filed Dec. 4, 2002, now U.S. Pat. No. 6,609,069; U.S. patent application Ser. No. 09/997,221, filed Nov. 28, 2001, now U.S. Pat. No. 6,587,798; and U.S. patent application Ser. No. 10/007,749, entitled "Fluid Parameter Measurement in Pipes Using Acoustic Pressures", filed Nov. 7, 2001, now U.S. Pat. No. 6,732,575, each of which are incorporated herein by reference.

In accordance with one embodiment of the present invention, the speed of sound propagating through the mixture 12 is measured by passively listening to the flow with an array of unsteady pressure sensors to determine the speed at which one-dimensional compression waves propagate through the mixture 12 contained within the pipe 14.

As shown in FIG. 16, an apparatus 310 embodying the present invention has an array of at least two acoustic pressure sensors 115,116, located at three locations $x_1,x_2$ axially along the pipe 14. One will appreciate that the sensor array may include more than two pressure sensors as depicted by pressure sensors 117,118 at location $x_3,x_N$. The pressure generated by the acoustic waves may be measured through pressure sensors 115–118. The pressure sensors 15–18 provide pressure time-varying signals $P_1(t),P_2(t),P_3(t),P_N(t)$ on lines 120,121,122,123 to a signal processing unit 130 to known Fast Fourier Transform (FFT) logics 126,127, 128,129, respectively. The FFT logics 126–129 calculate the Fourier transform of the time-based input signals $P_1(t)$–$P_N(t)$ and provide complex frequency domain (or frequency based) signals $P_1(\omega),P_2(\omega),P_3(\omega),P_N(\omega)$ on lines 132,133, 134,135 indicative of the frequency content of the input signals. Instead of FFT's, any other technique for obtaining the frequency domain characteristics of the signals $P_1(t)$–$P_N(t)$, may be used. For example, the cross-spectral density and the power spectral density may be used to form a frequency domain transfer functions (or frequency response or ratios) discussed hereinafter.

The frequency signals $P_1(\omega)$–$P_N(\omega)$ are fed to an array processing unit 138 which provides a signal to line 40 indicative of the speed of sound of the mixture $a_{mix}$, discussed more hereinafter. The $a_{mix}$ signal is provided to an entrained gas processing unit 142, similar to the processing unit 25, which converts $a_{mix}$ to a percent composition of a mixture and provides a gas volume fraction or % Comp signal to line 44 indicative thereof (as discussed hereinafter).

The data from the array of sensors 115–118 may be processed in any domain, including the frequency/spatial domain, the temporal/spatial domain, the temporal/wave-number domain or the wave-number/frequency (k-ω) domain. As such, any known array processing technique in any of these or other related domains may be used if desired, similar to the techniques used in the fields of SONAR and RADAR.

Figure 17:
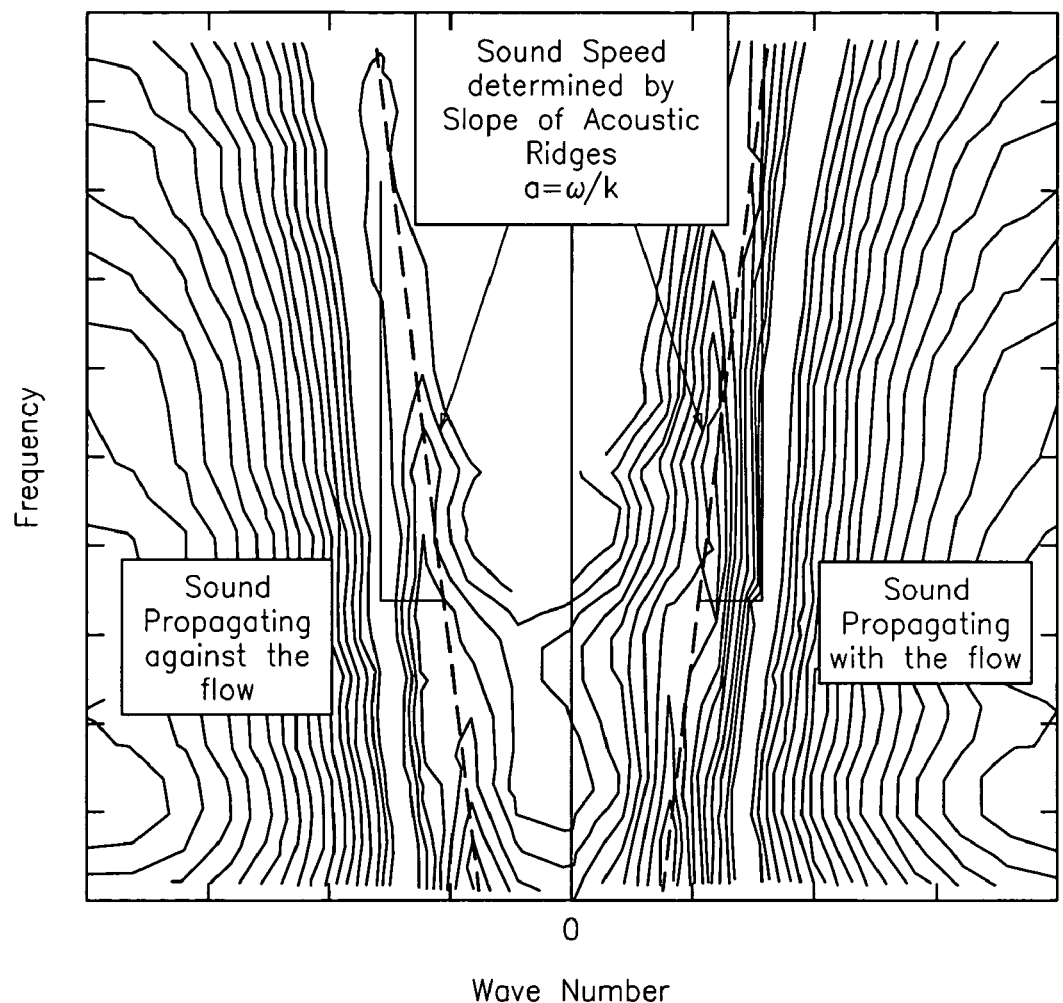
FIG. 17 a kω plot of data processed from an apparatus embodying the present invention that illustrates slope of the acoustic ridges traveling in both directions of the pipe, in accordance with the present invention.

One such technique of determining the speed of sound propagating through the flow 12 is using array processing techniques to define an acoustic ridge in the k-ω plane as shown in FIG. 17. The slope of the acoustic ridge is indicative of the speed of sound propagating through the flow 12. This technique is similar to that described in U.S. Pat. No. 6,587,798 filed Nov. 28, 2001, titled "Method and System for Determining The Speed of Sound in a Fluid Within a Conduit", which is incorporated herein by reference. The speed of sound (SOS) is determined by applying sonar arraying processing techniques to determine the speed at which the one dimensional acoustic waves propagate past the axial array of unsteady pressure measurements distributed along the pipe 14.

The signal processor 24 performs a Fast Fourier Transform (FFT) of the time-based pressure signals $P_1(t)$–$P_N(t)$ to convert the pressure signal into the frequency domain. The power of the frequency-domain pressure signals are then determined and defined in the k-ω plane by using array processing algorithms (such as Capon and Music algorithms). The acoustic ridge in the k-ω plane, as shown in the k-ω plot of FIG. 17, is then determined. The speed of sound (SOS) is determined by measuring slope of the acoustic ridge. The gas volume fraction is then calculated or otherwise determined, as described hereinafter.

The flow meter of the present invention uses known array processing techniques, in particular the Minimum Variance, Distortionless Response or other adaptive array processing techniques (MVDR, Music, or Capon technique), to identify pressure fluctuations, which convect with the materials flowing in a conduit and accurately ascertain the velocity, and thus the flow rate, of said material. These processing techniques utilize the covariance between multiple sensors 18–21 at a plurality of frequencies to identify signals that behave according to a given assumed model; in the case of the apparatus 310, a model, which represents pressure variations 20 convecting at a constant speed across the pressure sensors comprising the flow meter monitoring head 12.

Also, some or all of the functions within the processor 130 may be implemented in software (using a microprocessor or computer) and/or firmware, or may be implemented using analog and/or digital hardware, having sufficient memory, interfaces, and capacity to perform the functions described herein.

Figure 18:
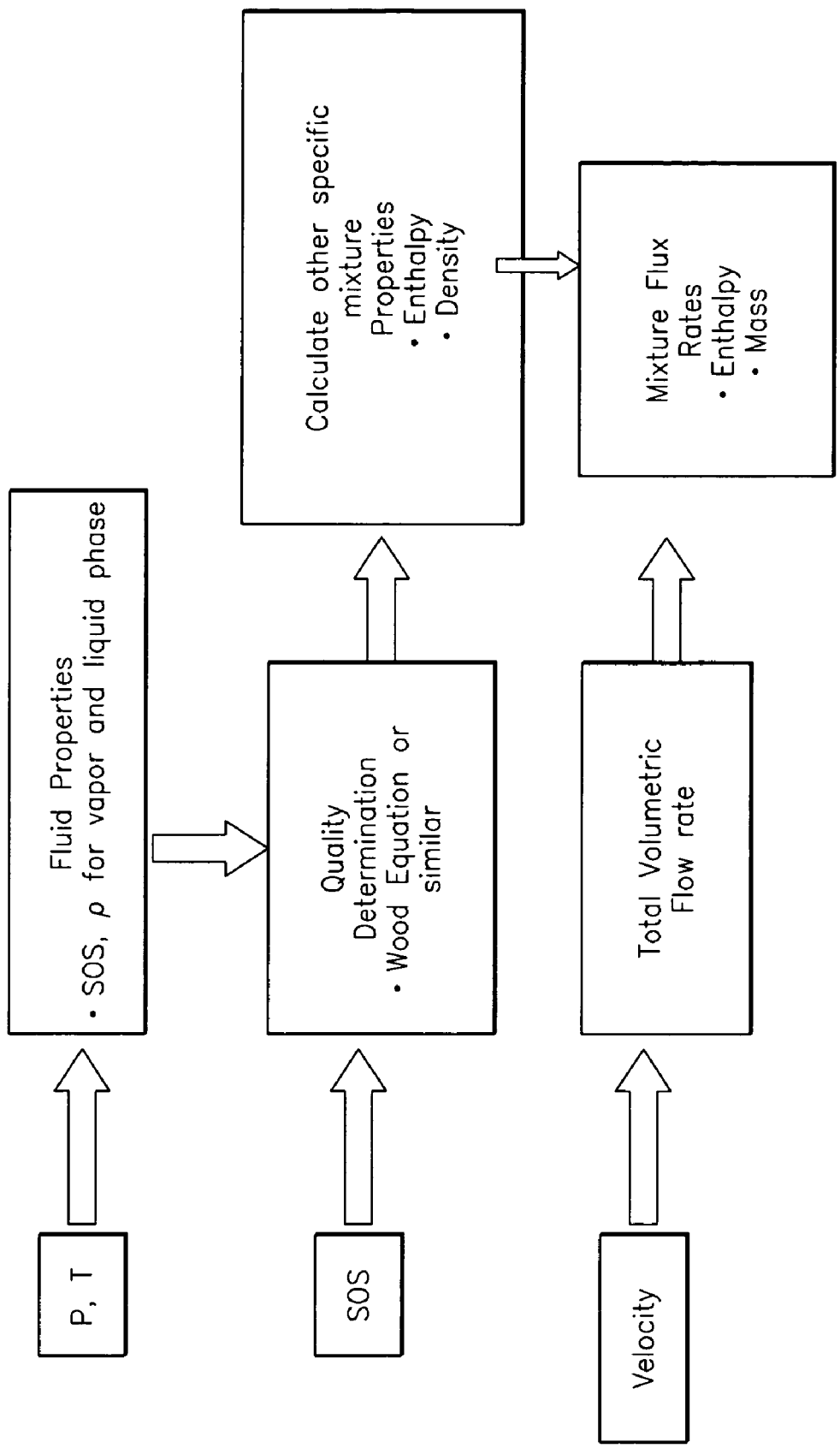
FIG. 18 is a functional diagram of an apparatus embodying the present invention.

FIG. 18 illustrates flow diagram representative of the apparatus 310 of FIG. 16.

Referring to FIGS. 4–7, while the plurality of sensors 23 of each pressure sensor 18–21 is described as a piezoelectric film (PVDF), the present invention contemplates that any sensor (such as a pressure sensor and/or strain sensor) may be used.

Figure 19:
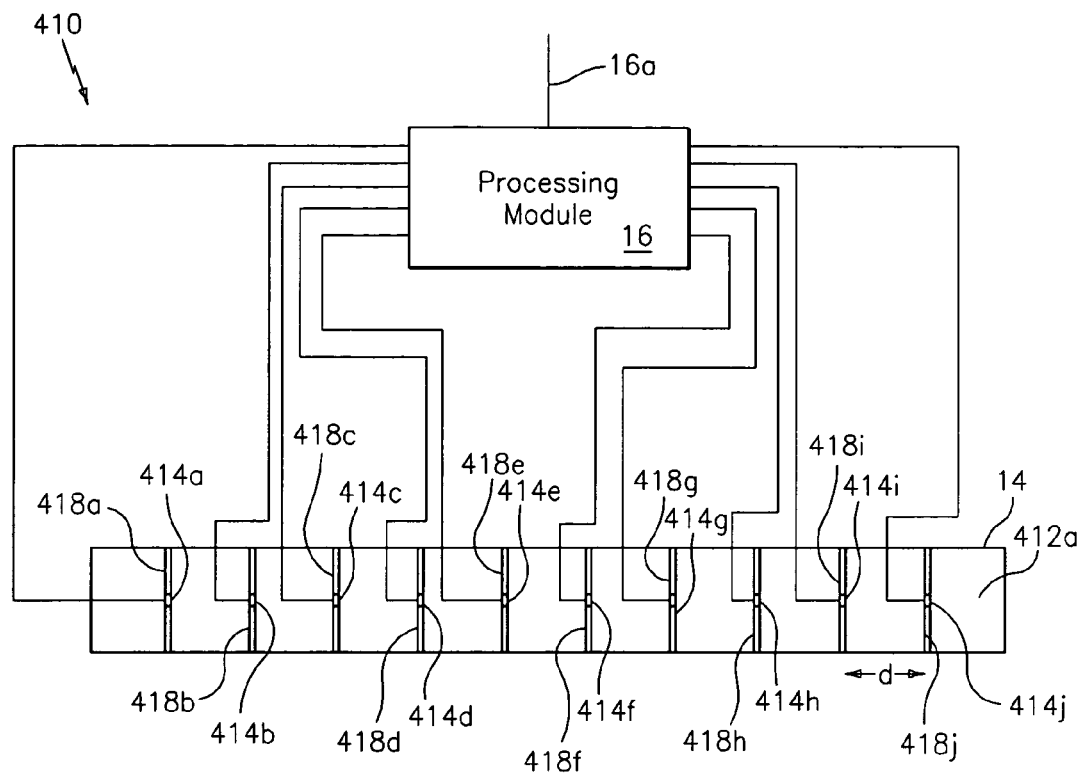
FIG. 19 is a diagram of an apparatus for determining internal pressure changes in a pipe in accordance with the present invention.

One such embodiment of the present invention is shown in FIGS. 19–30. FIG. 19 shows an apparatus generally indicated as 410 for determining internal pressure changes in a pipe 12. The apparatus features at least one sensor 414a, 414b, 414c, 414d, 414e, 414f, 414g, 414h, 414i, 414j and a processor module 16. In operation, the at least one sensor 414a, 414b, 414c, 414d, 414e, 414f, 414g, 414h, 414i, 414j is coupled to an outer surface 12a of a pipe 12 by a coupling arrangement 418a, 418b, 418c, 418d, 418e, 418f, 418g, 418h, 418i, 418j and responds to radial expansion and contraction of the pipe 12 caused by internal pressure changes of a medium flowing therein, for providing a sensor signal containing information about the radial expansion and contraction of the pipe 12. The processor module 16 responds to the sensor signal, for providing a processor module signal along line 16a containing information about the internal pressure changes of the medium flowing in the pipe 12.

Figure 20:
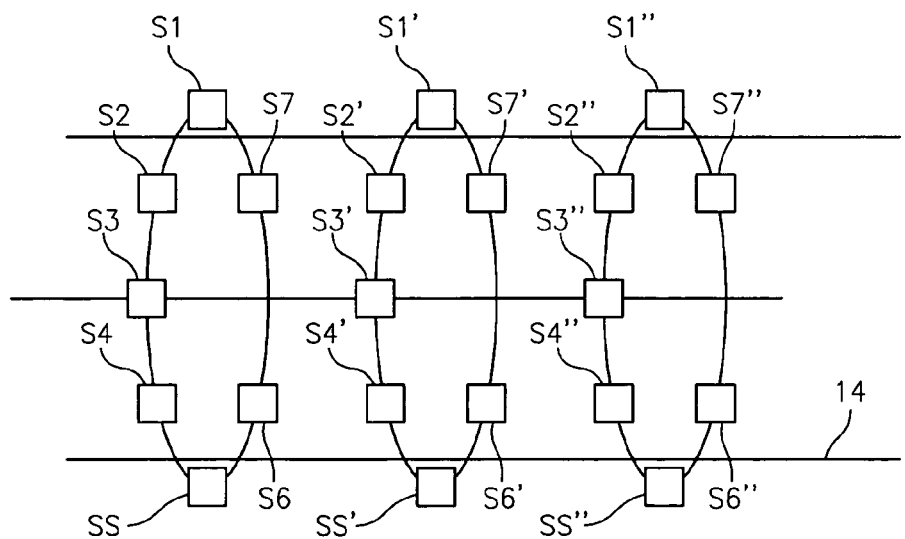
FIG. 20 is a diagram showing pressure sensors arranged axially and circumferentially on a pipe in accordance with the present invention.

The at least one sensor includes a plurality or multiplicity of strain sensors 414a, 414b, 414c, 414d, 414e, 414f, 414g, 414h, 414i, 14j that are arranged axially at locations along the length of the pipe. The plurality or multiplicity of strain sensors 414a, 414b, 414c, 414d, 414e, 414f, 414g, 414h, 414i, 14j may also be circumferentially arranged around the pipe like sensors $S_1, S_2, S_3, \ldots, S_6; S_1', S_2', S_3', \ldots, S_6';$ and $S_1'', S_2'', S_3'', \ldots, S_6''$ at each location, as best shown in FIG. 20. The set of strain sensors 414a, 414b, 414c, 414d, 414e, 414f, 414g, 414h, 414i, 14j spaced axially at locations along the length of the pipe enable one to determine either an acoustic or vortical/convective ridge to measure the speed of sound or the velocity of the flow, respectively. The multiplicity of strain sensors 414a, 414b, 414c, 414d, 414e, 414f, 414g, 414h, 414i, 414j are separated from one another by a predetermined distance d.

Figure 21:
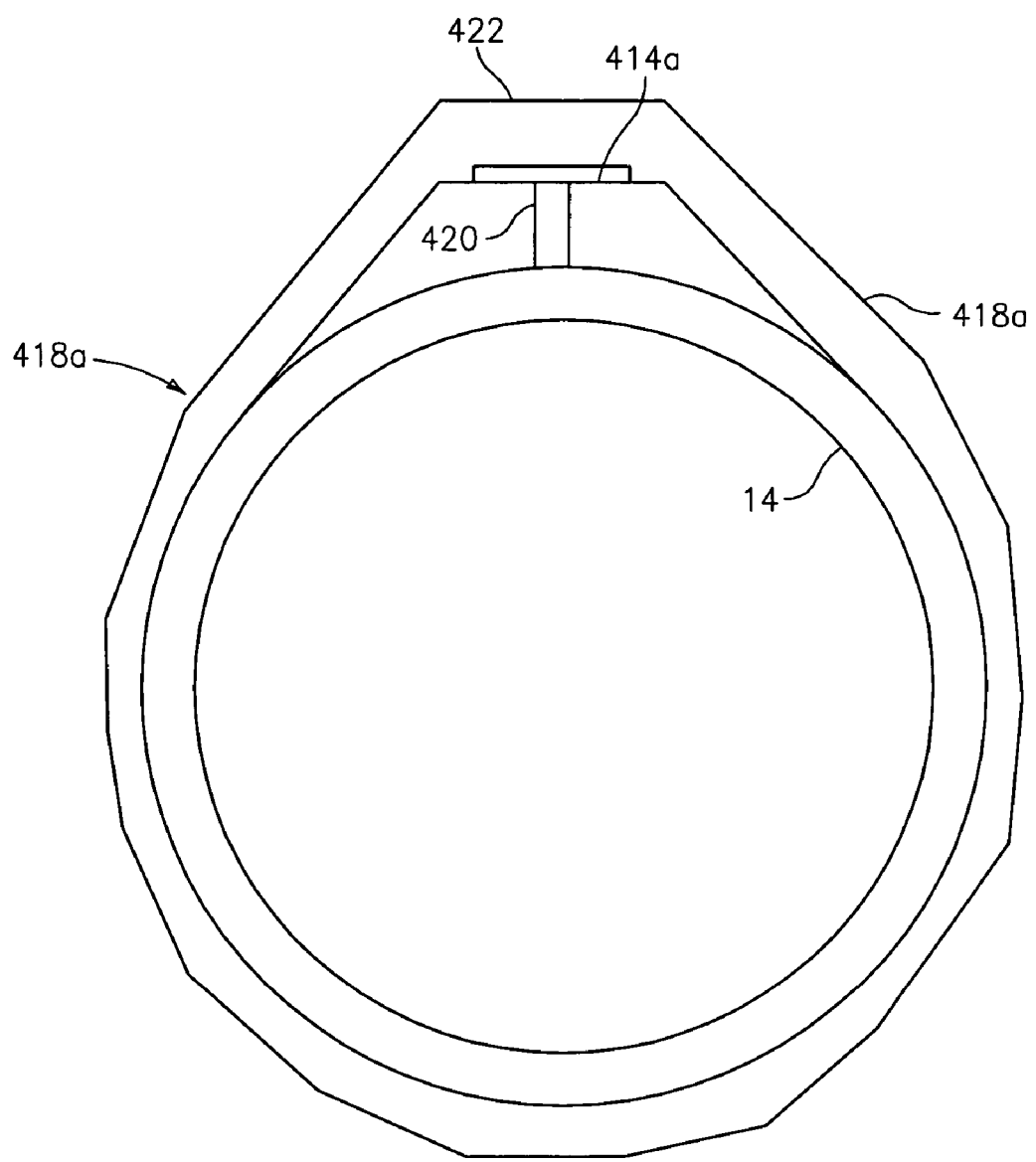
FIG. 21 is a diagram of one sensor arranged on a pipe in accordance with the present invention.

As shown in FIG. 21, the at least one sensor may include a strain sensor 14a which may be a spring element or transducer in the form of a diaphragm that is coupled capacitively to another surface of the transducer so that pipe radial growth causes a displacement in the diaphragm which is sensed as a change in capacitance between the diaphragm and the other surface. Embodiments are also envisioned using a diaphragm in a resistive-based configuration. The at least one sensor may also include a PCB load cell or a piezoelectric or magnetostrictive structure which provides a voltage or charge when strained. Embodiments are envisioned using many different types of strain sensor, including sensing based on shearing strain, Poisson strain, bending or moment strain, as well as sensors that are measured by mechanical, optical, acoustic, pneumatic and electrical means. The scope of the invention is not intended to be limited to the type or kind of strain sensor used. For example, see U.S. Pat. No. 6,463,813, which discloses a displacement based pressure sensor, which is hereby incorporated by reference in its entirety.

In FIG. 21, the coupling arrangement is shown as an outer strap, metal band or hose clamp 418a, wherein the at least one sensor 14a is loaded against the outer surface 412a of the pipe 12 by the outer strap 418a. Alternatively, the at least one sensor may be affixed directly to the outer surface of the pipe. See FIG. 23. Alternatively, the apparatus may include a mechanical link 20 arranged between the at least one sensor 414a and the surface of the pipe 412a, as well as a block 422 arranged between the outer strap 418a and the at least one sensor 414a. In this case, the mechanical link or mass is arranged between the at least one sensor 414a and the outer strap 418a. In operation, the movement of the mechanical link or mass is sensed to determine the unsteady pressures of the process flow in the pipe. The sensors may be mounted directly on the inside or the outside of the strap 418a that is itself mounted on the outer surface of the pipe so as to measure the hoop strain or breathing mode of the pipe. Embodiments are envisioned using many different strapping techniques for holding the sensor in relation to the outer surface of the pipe. The scope of the invention is not intended to be limited to any particular strapping or clamping technique.

Figure 22:
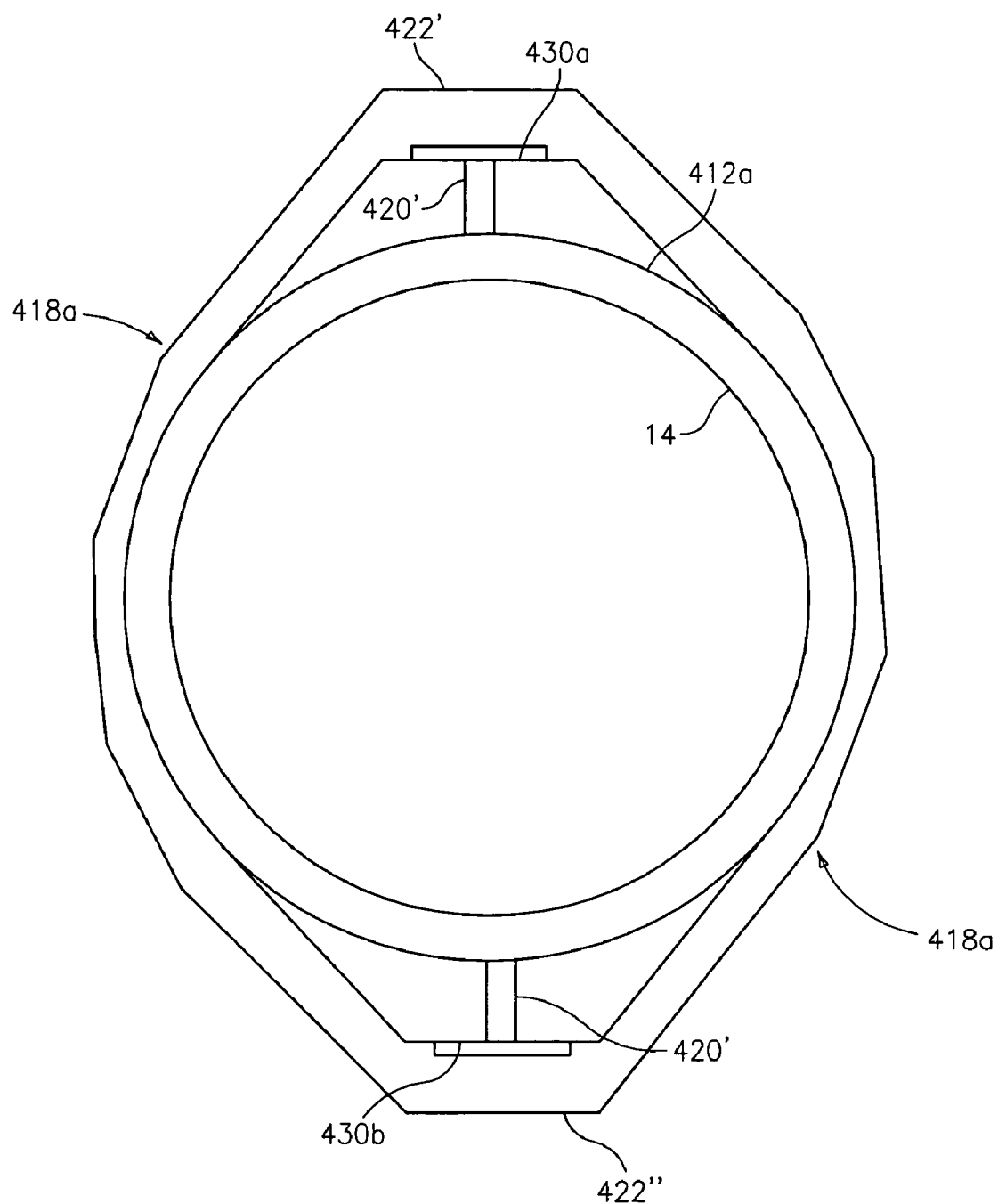
FIG. 22 is a diagram of two diametrically arranged sensors arranged on a pipe in accordance with the present invention.

FIG. 22 shows an alternative embodiment, wherein the at least one sensor includes two strain sensors 430a, 430b diametrically opposed on the outer surface 412a of the pipe 12 to compensate for bending modes caused by the flexing of the pipe 12. In effect, the strain sensor on the opposing side of the pipe 12 cancels everything out but the breathing mode of the pipe 12. As shown, the apparatus includes mechanical links 20', 20" arranged between the at least one sensor 430a, 430b and the surface of the pipe 412a, as well as blocks 422', 422" arranged between the outer strap 18a and the at least one sensor 430a, 430b.

Figure 23:
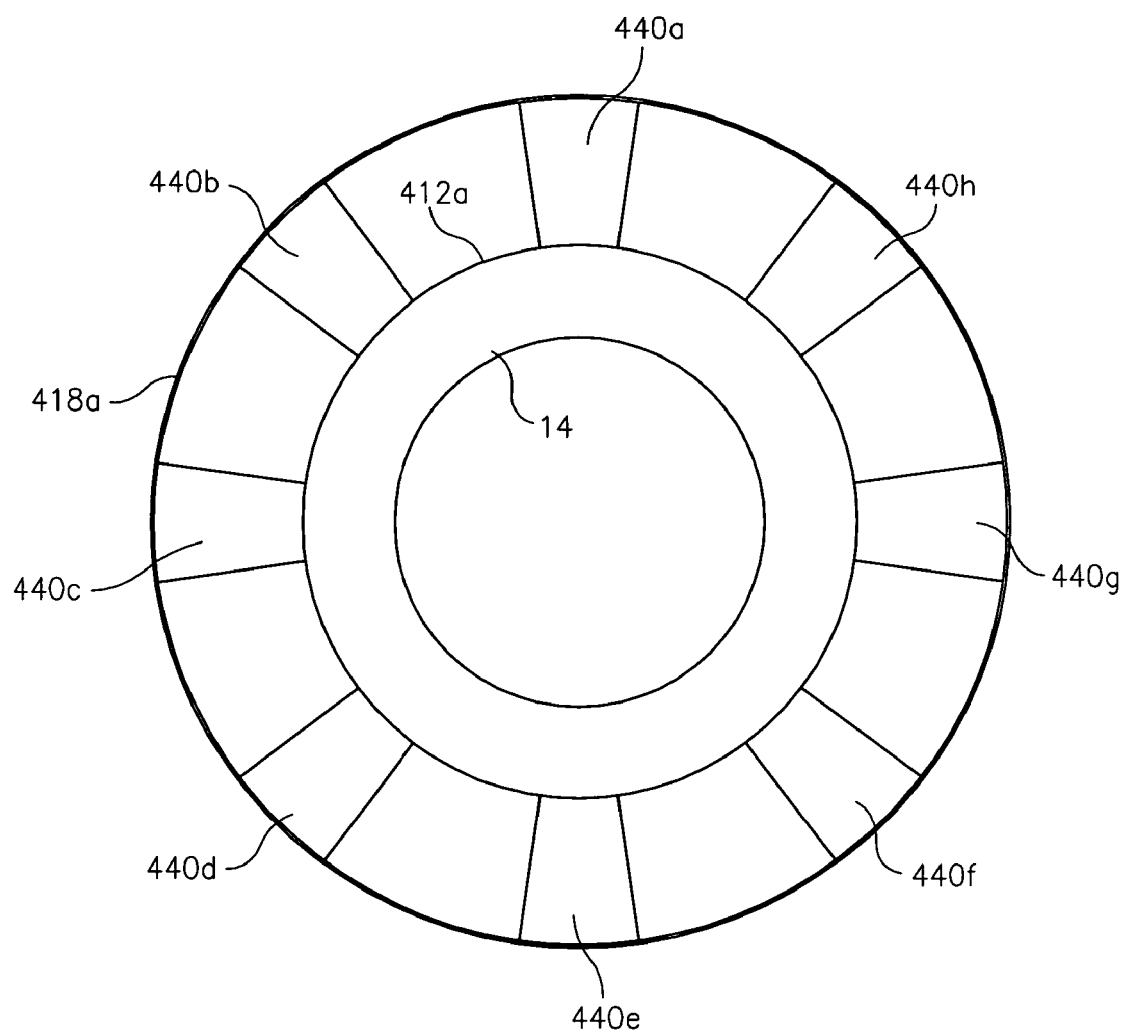
FIG. 23 is a diagram of a multiplicity of sensors arranged equi-distant around a pipe in accordance with the present invention.

FIG. 23 shows an alternative embodiment, wherein the at least one sensor includes a multiplicity of strain sensors 440a, 440b, 440c, 440d, 440e, 440f, 440g, 440h arranged equi-distantly around the outer surface 412a of the pipe 12 to filter or compensate for bending modes caused by the flexing of the pipe. Embodiments are envisioned in which the sensors are arranged in many different configurations in relation to the outer surface of the pipe, including a non-equi-distant configuration. The scope of the invention is not intended to be limited to the manner of displacing or arranging the sensors on the outer surface of the pipe.

The sensor element may be facing away from the outer surface of the pipe or facing the outer surface of the pipe. The scope of the invention is not intended to be limited to the direction that the sensor element is facing. In embodiments in which the sensor element may be facing away from the outer surface of the pipe, a compensation may have to be made in relation to the phase of the sensed signal.

Figure 24:
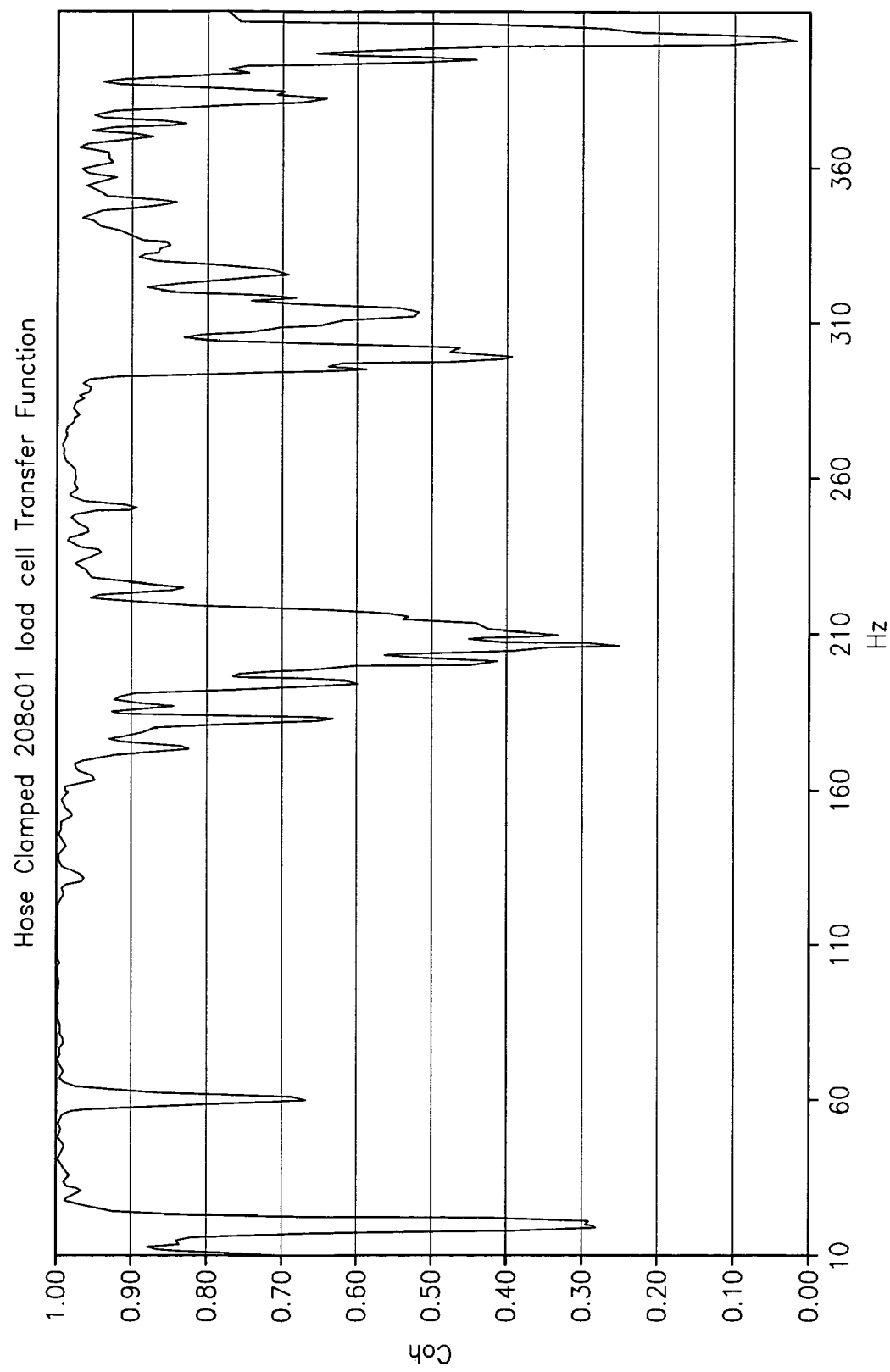
FIG. 24 is a plot of hose clamped load cell coherence with a ported pressure sensor in accordance with the present invention.

FIG. 24 shows a plot of hose clamped load cell coherence with a ported pressure sensor. In an experiment, a ported PCB pressure sensor was arranged in a pipe, and arranged a single banded PCB load cell arranged on the outside of the pipe in the same location. The ported PCB pressure sensor provides a direct measurement of the unsteady pressures in the process flow in the pipe. The single banded PCB load cell arranged on the outside of the pipe provides a corresponding measurement of the unsteady pressures in the process flow in the pipe. Then the reference signal is compared with the ported pressure sensor signal and when the reference data is equal to the test data then the plot shows a coherence of 1.0, when the two differ one gets a coherence less than 1.0. The plot shows good coherence between the experimental sensor and the ported sensor.

Figure 25:
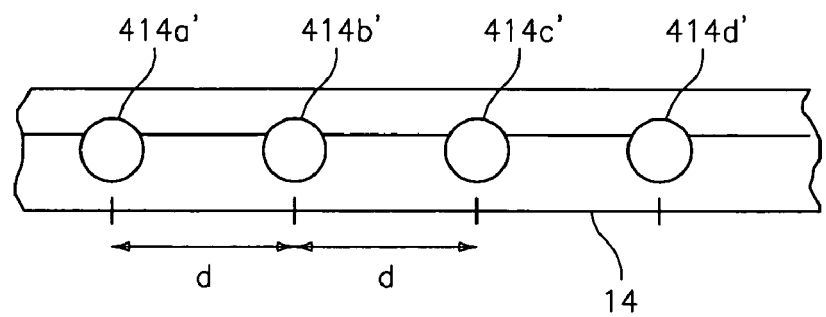
FIG. 25 is a diagram of an alternative embodiment in which one or more sensors are mounted directly on an outer surface of a pipe in accordance with the present invention.

FIG. 25 shows an embodiment in which the sensors 414a', 414b', 414c', 414d' are mounted directly on the outer surface of the pipe 12, for example, by glue or epoxy.

Radial Growth is Correlated with Internal Pressures

In relation to FIG. 21, testing has shown that internal pressures are correlated to a measurement of radial growth of pipe outer diameter (OD) through the use of the aforementioned strain sensing devices. The displacements of the pipe OD are so small that measurement of them can be accomplished by means typically reserved for measurement of stress and strain in a material. For example, an experiment conducted using an off-the-shelf Piezoelectric crystal based load cell 208C1 from a company known as PCB and either a stiff U-clamp outer ring or less stiff ring created by a 0.025" thick hose clamp (FIG. 21) confirmed that there is correlation between internal pressures measured with a PCB 102M206 pressure transducer and the signals arising from the load cell. The experiment was conducted on an 8" diameter schedule 10 standpipe filled with water and with a bubbler for a sound (dynamic pressure) source.

The term "ring" is used loosely here; any structure that is supported by the pipe and circumferentially surrounds the pipe constitutes a ring.

Figure 26:
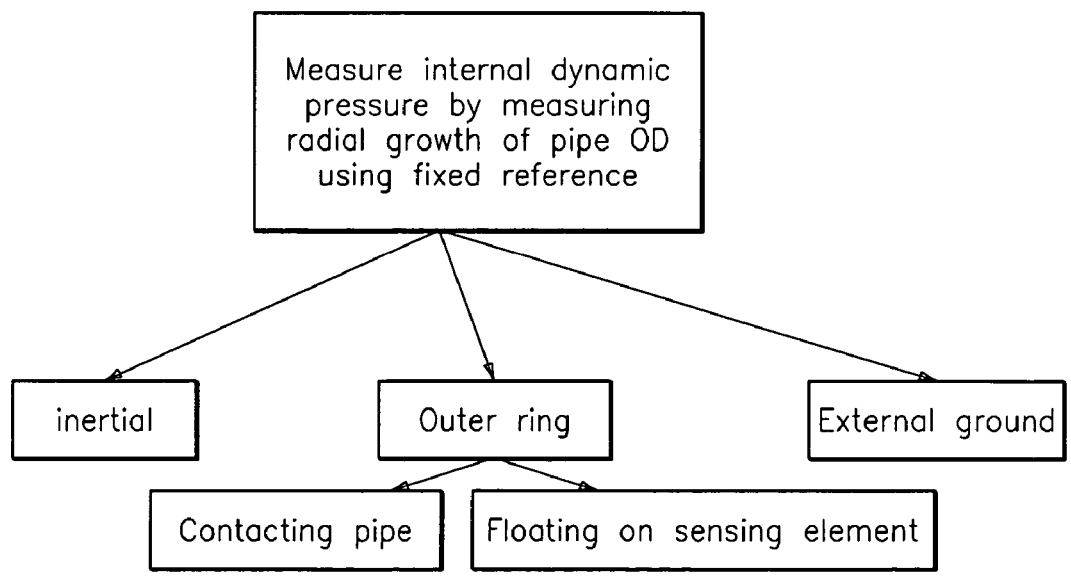
FIG. 26 is a diagram showing different strategies for measuring internal dynamic pressure in a pipe in accordance with the present invention.
Figure 27:
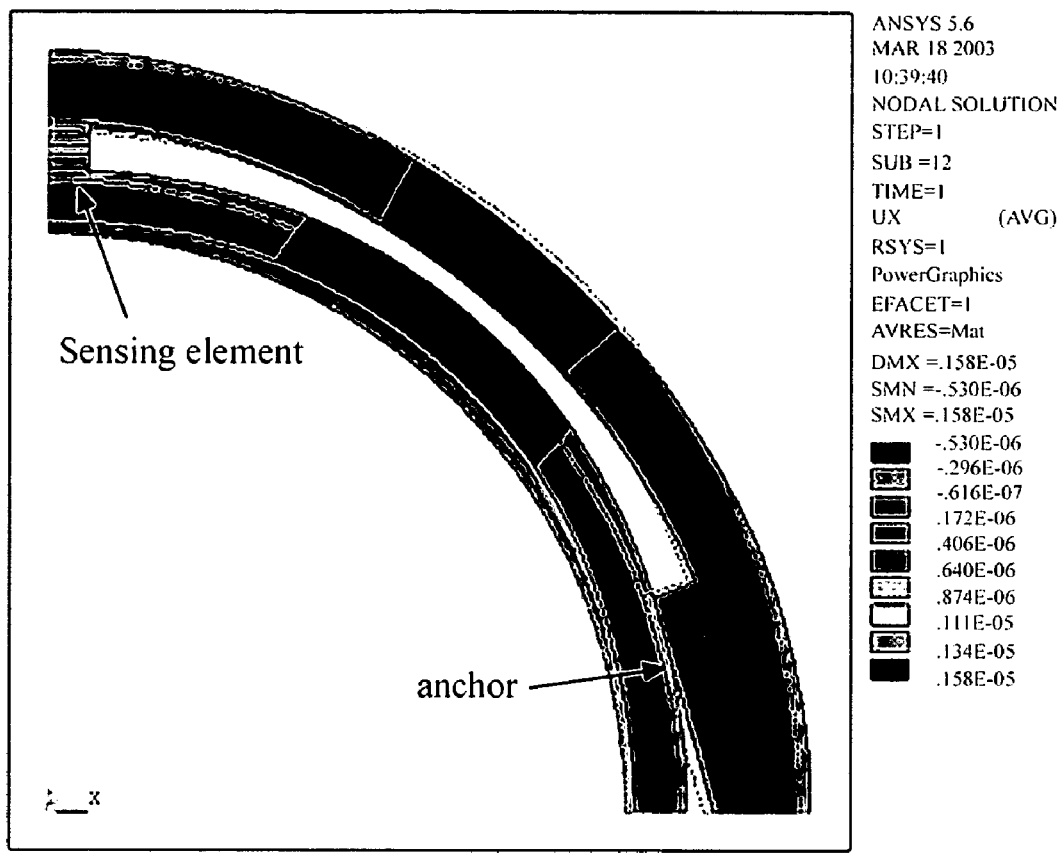
FIG. 27 is a one quarter cross sectional view of a sensing element diagram arranged in relation to a pipe in accordance with the present invention.
Figure 28:
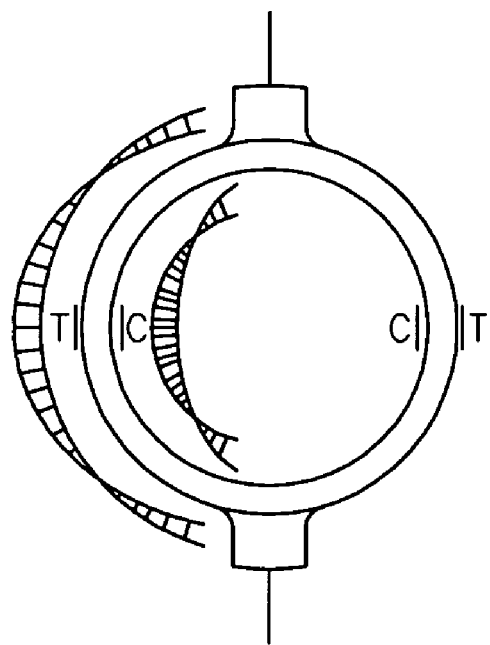
FIG. 28 is a diagram of a ring configuration in accordance with the present invention.

FIGS. 26–28: Radial Growth can be Measured in Numerous Ways

If a fixed ring is attached to the pipe OD, either through a sensing element or directly to the pipe, then the ring forms a reference point and motion between the ring and the pipe OD can be measured with an array of transducers arranged circumferentially (FIG. 26). A load cell is an example of a sensing element for making such a measurement.

If the sensing elements support the pipe then all radial growth goes into strain of a sensing element, but the outer ring can subject the sensing elements to transverse inertial loads. If, on the other hand, the ring is anchored to the pipe wall in locations, then transverse loads originating from inertial forces on the outer ring are to some degree absorbed by the pipe wall (FIG. 26). In addition, modeling suggests that constraining the pipe wall at points through anchors causes amplified deflection of the pipe wall 90 degrees from this point, resulting in increased sensitivity. The mass of the outer ring should be minimized so as to minimize the deformations in the pipe resulting from reacting the inertial forces of the outer ring.

The sensing element can be placed either between the outer ring and the pipe OD as in FIG. 27 or incorporated into the outer ring itself in a tangential orientation so as to measure the hoop stress in the ring.

Yet another approach would be to measure bending stress in the outer ring as shown in FIG. 28, using a Morehouse ring. The strain distribution in the ring is a complex function of the geometry, and is significantly affected by the design details of the bosses, but the distribution illustrated in the figure is reasonably representative for constant-thickness rings. Because the bending moment does not vary significantly in the region of the horizontal diameter, the strain distribution is nearly uniform in this area. The strain can be measured with strain gauges located at C (compression) and T (tension) positions.

Simple Ring Configuration Based on Classical Morehouse Proving Ring Principle.

If the outer ring is not supported by the pipe but instead attached to an external point then radial growth of the pipe OD could also be measured with, for instance, a load cell. This approach is not at all preferred given that one needs to be concerned both with the motion of the pipe and the motion of the external reference point.

Radial growth could also be measured by attaching an inertial mass to the sensing element. The mass resists motion created by the radial growth of the pipe OD, and does this through the sensing element. An accelerometer is an example of such an inertial mass and sensing element. The following web sight describes an accelerometer that uses capacitance as the sensing element. A plurality of these could be arranged around the circumference to measure radial displacement.

The Key elements of design are as follows:

Maximize sensitivity to internal pressure fluctuations

Minimize mass of fixed reference

Maximize stiffness of fixed reference

Monitor as much of the circumference as possible

Sensitivity should be maximized in order to maximize signal to noise. Noise could arise from electrical sources or form mechanical sources not associated with the internal pipe pressure.

It is important to negate all signals except those associated with OD growth arising from internal pressures. For instance, signals could arise from inertial forces generated in the outer ring associated with vibration of the pipe centerline. Adding the signals from sensing points at 180 degree locations would tend to negate these signals and enforce signals from OD growth. FIG. 28 shows an arrangement of an op amp configured as an adder circuit that could accomplish this.

Also, if the outer ring is high in mass or low in stiffness it could have vibration modes in a frequency of interest that contribute signals not associated with pipe wall growth.

It is important to incorporate as much of the circumferential strain in the pipe as possible. It is therefore of benefit to implement a plurality of sensing points around the pipe. These points can be combined into one signal representing the radial growth (and ultimately the internal dynamic pressure) using a circuit like that shown in FIG. 23.

Means of Measurement: Piezoelectric

When strain is applied to a quartz crystal, a charge is developed across the crystal that is proportional to the strain. The fundamental difference between these crystal sensors and static-force devices such as strain gages is that the electric signal generated by the crystal decays rapidly. This characteristic makes these sensors unsuitable for the measurement of static forces or pressures but useful for dynamic measurements.

Piezoelectric transducers have a high modulus and can be structurally very stiff.

A piezoelectric force sensor is almost as rigid as a comparably proportioned piece of solid steel. This stiffness and strength allows these sensors to be directly inserted into machines as part of their structure. Their rigidity provides them with a high natural frequency. To ensure accurate measurement, the natural frequency of the sensing device must be substantially higher than the frequency to be measured. They have a large dynamic range so very small to very large stress can be measured.

Some synthetic piezocrystals (E.G. K15 from Keramos), and pure quartz as well, have high operating temperatures (>500F), allowing use in high temperature flow measurements like steam.

Strain-Gage:

Load cells convert the load acting on them into electrical signals. The gauges themselves are bonded onto a beam or structural member that deforms when load is applied. In most cases, four strain gages are used to obtain maximum sensitivity and temperature compensation. Two of the gauges are usually in tension, and two in compression, and are wired with compensation adjustments as shown in FIG. 26. When weight is applied, the strain changes the electrical resistance of the gauges in proportion to the load.

Piezoresistive:

Similar in operation to strain gages, piezoresistive sensors generate a high level output signal, making them ideal for simple weighing systems because they can be connected directly to a readout meter. The availability of low cost linear amplifiers has diminished this advantage, however. An added drawback of piezoresistive devices is their nonlinear output.

Inductive and Reluctance:

Both of these devices respond to displacement of a ferromagnetic core. One changes the inductance of a solenoid coil due to the movement of its iron core; the other changes the reluctance of a very small air gap.

Magnetostrictive:

The operation of this sensor is based on the change in permeability of ferromagnetic materials under applied stress. It is built from a stack of laminations forming a load-bearing column around a set of primary and secondary transformer windings. When a load is applied, the stresses cause distortions in the flux pattern, generating an output signal proportional to the applied load. This is a rugged sensor and continues to be used for force and weight measurement in rolling mills and strip mills.

Figure 29:
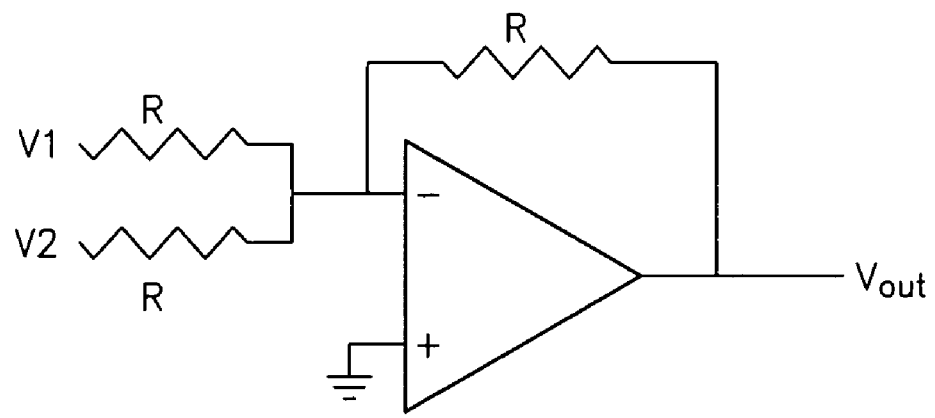
FIG. 29 shows an arrangement of an op amp configured as an adder circuit in accordance with the present invention.

Capacitive:

Capacitance sensors may be used. This capacitance change results from the movement of a diaphragm element (FIGS. 27–29). In a capacitance-type pressure sensor, a high-frequency, high-voltage oscillator is used to charge the sensing electrode elements. In a two-plate capacitor sensor design, the movement of the diaphragm between the plates is detected as an indication of the changes in process pressure.

As shown in FIG. 27–29, the deflection of the diaphragm causes a change in capacitance that is detected by a bridge circuit. This circuit can be operated in either a balanced or unbalanced mode. In balanced mode, the output voltage is fed to a null detector and the capacitor arms are varied to maintain the bridge at null. Therefore, in the balanced mode, the null setting itself is a measure of diaphragm deflection. When operated in unbalanced mode, the deflection is related to the ratio between the output voltage and the excitation voltage.

Single-plate capacitor designs are also common. In this design, the plate is located on the back side of the diaphragm and the variable capacitance is a function of deflection of the diaphragm.

Capacitance-type sensors are quite responsive; because the distance the diaphragm must physically travel is only a few microns.

Optical:

This web sight shows an example of an extremely sensitive optical transducer. There are a number of other approaches.

There are a number of other methods of making sensitive measurements of motion. This text describes a number of pressure transducer designs that could also be applied to pipe wall deflection measurement.

Finally, the outer ring need not be limited to each axial position. A shell around the pipe could act as a continuous ring along the length of the array. It is supported by the pipe at the ends outside the array, as shown in FIG. 30.

The Processor Module 16

The processor module 16 may be implemented using hardware, software, or a combination thereof. The scope of the invention is not intended to be limited to any particular implementation thereof. For example, a typical software implementation may include using a microprocessor architecture having a microprocessor, a random access memory (RAM), a read only memory (ROM), input/out devices and a control, address and databus for connecting the same. Embodiments are envisioned in which the processor module 16 is implemented in many different ways by a person skilled in the art. The scope of the invention is not intended to be limited to any particular implementation of the processor module 16. For example, U.S. patent application ser. No. 09/344,094 filed Jun. 25, 1999, entitled "Fluid Parameter Measurement in Pipes Using Acoustic net Pressure", now U.S. Pat. No. 6.354.147, and U.S. patent application ser. No. 09/344,093 filed Jun. 25, 1999, , entitled "Non-Intrusive Fiber Optic Pressure Sensor for Measuring Unsteady Pressures within a Pipe", now U.S. Pat. No. 6,450,037, disclose techniques for responding to one or more sensed signals, for providing a resulting signal containing information about the internal pressure changes in the pipe, both hereby incorporated by reference in their entirety.

The scope of the invention is also intended to include substituting an accelerometer for the sensor and using it to create a portable instrument for measuring entrained air in a medium flowing in the pipe, such as a pulp.

For certain types of pressure sensors, e.g., pipe strain sensors, accelerometers, velocity sensors or displacement sensors, discussed hereinafter, it may be desirable for the pipe 14 to exhibit a certain amount of pipe compliance.

The pressure sensors 23 described herein may be any type of pressure sensor, capable of measuring the unsteady (or ac or dynamic) pressures within a pipe, such as piezoelectric, optical, capacitive, resistive (e.g., Wheatstone bridge), accelerometers (or geophones), velocity measuring devices, displacement measuring devices, etc. If optical pressure sensors are used, the sensors 23 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702, which are incorporated herein by reference. Alternatively, the sensors 23 may be electrical or optical strain gages attached to or embedded in the outer or inner wall of the pipe which measure pipe wall strain, including microphones, hydrophones, or any other sensor capable of measuring the unsteady pressures within the pipe 14. In an embodiment of the present invention that utilizes fiber optics as the pressure sensors 23 they may be connected individually or may be multiplexed along one or more optical fibers using wavelength division multiplexing (WDM), time division multiplexing (TDM), or any other optical multiplexing techniques.

For any of the embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe 14. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe 14 if desired.

It is also within the scope of the present invention that any other strain sensing technique may be used to measure the variations in strain in the pipe, such as highly sensitive piezoelectric, electronic or electric, strain gages attached to or embedded in the pipe 14.

In certain embodiments of the present invention a piezoelectronic pressure transducer may be used as one or more of the pressure sensors 23 and it may measure the unsteady (or dynamic or ac) pressure variations inside the pipe 14 by measuring the pressure levels inside of the pipe 14. In an embodiment of the present invention the sensors 23 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

The pressure sensors 23 described herein may be any type of pressure sensor, capable of measuring the unsteady (or ac or dynamic) pressures within a pipe, such as piezoelectric, optical, thermal, capacitive, inductive, resistive (e.g., Wheatstone bridge), accelerometers (or geophones), velocity measuring devices, displacement measuring devices, etc. If optical pressure sensors are used, the sensors 23 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702. Alternatively, the sensors 23 may be electrical or optical strain gages attached to or embedded in the outer or inner wall of the pipe which measure pipe wall strain, including microphones, hydrophones, or any other sensor capable of measuring the unsteady pressures within the pipe 14. In an embodiment of the present invention that utilizes fiber optics as the pressure sensors 23, they may be connected individually or may be multiplexed along one or more optical fibers using wavelength division multiplexing (WDM), time division multiplexing (TDM), or any other optical multiplexing techniques.

A piezo-electronic pressure transducer may be used (or alternatively even a common strain gage may be used) as one or more of the pressure sensors 23, and it may measure the unsteady (or dynamic or ac) pressure variations Pin inside the pipe 14 by measuring the pressure levels (or for the strain gage, the elastic expansion and contraction of the diameter of the pipe 14. In an embodiment of the present invention the sensors 23 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

For any of the embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe 12. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe 12 if desired.

It is also within the scope of the present invention that any other strain sensing technique may be used to measure the variations in strain in the pipe, such as highly sensitive piezoelectric, electronic or electric, strain gages attached to or embedded in the pipe 12.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring at least one parameter of a fluid flowing within a pipe, comprising:
   a spatial array of at least two sensors, disposed at different axial locations along the pipe, and each sensor measuring a parameter within the pipe at each corresponding axial location, each of said sensors providing a signal indicative of a parameter within the pipe at said axial location of a corresponding one of said sensors, each sensor including at least two sensing elements disposed circumferentially at said corresponding axial location; and
   a signal processor, responsive to said signals, which provides a signal indicative of the at least one parameter of the fluid in the pipe.

2. The apparatus of claim 1, wherein the at least two sensors are pressure sensors that provide a signal indicative of the unsteady pressure within the pipe, and wherein the sensing elements are pressure sensitive.

3. The apparatus of claim 2, wherein the sensing elements of each pressure sensor are spaced circumferentially around the pipe at the corresponding axial location.

4. The apparatus of claim 1 wherein each sensor measures an acoustic pressure and provides a signal indicative of an acoustic noise within the pipe.

5. The apparatus of claim 1, wherein the signal processor, responsive to said pressure signals, provides a signal indicative of the speed of sound propagating through the fluid in the pipe.

6. The apparatus of claim 5 wherein said signal processor comprises logic, which calculates a speed at which sound propagates along said spatial array.

7. The apparatus of claim 5 wherein said signal processor comprises logic, which calculates a frequency based signal for each of said acoustic pressure signals.

8. The apparatus of claim 6 wherein said acoustic pressure signals each comprise a frequency based signal and wherein said signal processor comprises logic which calculates a ratio of two of said frequency based signals.

9. The apparatus of claim 1, wherein the spatial array comprises at least three of said sensors.

10. The apparatus of claim 5 wherein the signal processor comprises logic which determines at least one of a vapor/liquid composition, the wetness or steam quality (volumetric phase fraction), the volumetric flow rate, the size of the liquid particles, the mass flow, the enthalpy, density, the velocity of the mixture in the pipe, and the speed of sound propagating through the mixture in the pipe.

11. The apparatus of claim 1 wherein at least one of said pressure sensors measures strain on the pipe.

12. The apparatus of claim 5 wherein the frequency based sound speed is determined utilizing a dispersion model to determine the at least one parameter of the fluid.

13. The apparatus of claim 5 wherein the array of acoustic sensors are spaced sufficiently such that the entire length of the array is at least a significant fraction of a measured wavelength of the acoustic waves being measured.

14. The apparatus of claim 1 wherein at least one sensor provides a first filter which measures a vortical pressure field at a first axial location along the pipe and provides a first pressure signal indicative of said vortical pressure field; and
   at least a second sensor provides a second filter which measures said vortical pressure field at a second axial location along the pipe and provides a second pressure signal indicative of said vortical pressure field.

15. The apparatus of claim 1, wherein the signal processor, responsive to said signals indicative of a parameter within the pipe, provides a velocity signal indicative of a velocity of the said vortical pressure field moving in the pipe.

16. The apparatus of claim 14, wherein said first and said second filters filter out wavelengths associated with an acoustic pressure field and passes wavelengths associated with said vortical pressure field.

17. The apparatus of claim 16, wherein said first filter comprises a first spatial filter that includes at least a first and a second unsteady pressure sensors disposed a predetermined first distance apart from each other; and
   said second filter comprises a second spatial filter that includes at least a third and a fourth unsteady pressure sensors disposed a predetermined second distance apart from each other.

18. The apparatus of claim 1, wherein the sensing elements are a piezoelectric film sensor.

19. The apparatus of claim 1, wherein the sensors are clamped onto the pipe.

20. The apparatus of claim 1, wherein each sensor measures a pressure produced by a vortical disturbance in the fluid.

21. The apparatus of claim 14, wherein the signal processor defines a convective ridge to determine the at least one parameter of the fluid.

22. The apparatus of claim 14, wherein the at least one parameter of the fluid is the volumetric flow rate.

23. The apparatus of claim 21, wherein the at least one parameter of the fluid is the volumetric flow rate.

24. The apparatus of claim 1, wherein the sensors are disposed in the pipe and in contact with the fluid.

25. An apparatus for determining internal pressure changes of a medium flowing in a pipe, comprising:
   at least one sensor for coupling to an outer surface of a pipe by a coupling arrangement, responsive to radial expansion and contraction of the pipe caused by internal pressure changes of a medium flowing therein, for providing a sensor signal containing information about the radial expansion and contraction of the pipe;
   a processor module, responsive to the sensor signal, for providing a processor module signal containing information about the internal pressure changes of the medium flowing in the pipe.

26. The apparatus according to claim 25, wherein the at least one sensor includes a plurality of sensors.

27. The apparatus according to claim 26, wherein the plurality of sensors are arranged axially along the length of the pipe.

28. The apparatus according to claim 27, wherein the plurality of sensors are also circumferentially arranged around the pipe.

29. The apparatus according to claim 25, wherein the at least one sensor includes a strain sensor.

30. The apparatus according to claim 25, wherein the at least one sensor includes a spring element in the form of a diaphragm that is coupled capacitively to another surface of a transducer so that pipe radial growth causes a displacement in the diaphragm which is sensed as a change in capacitance between the diaphragm and the other surface.

31. The apparatus according to claim 25, wherein the coupling arrangement is an outer strap and the at least one sensor is loaded against the outer surface of the pipe by the outer strap.

32. The apparatus according to claim 31, wherein the apparatus includes either a mechanical link arranged between the at least one sensor and the outer surface of the pipe, a block arranged between the at least one sensor and the outer strap or a combination thereof.

33. The apparatus according to claim 25, wherein the at least one sensor includes a piezoelectric or magnetostrictive structure which provides a voltage or charge when strained.

34. The apparatus according to claim 25, wherein the at least one sensor include two strain sensors diametrically opposed on the outer surface of the pipe to compensate for bending modes caused by the flexing of the pipe.

35. The apparatus according to claim 25, wherein the at least one sensor include a multiplicity of strain sensors arranged equi-distantly around the outer surface of the pipe to filter or compensate for bending modes caused by the flexing of the pipe.

36. The apparatus according to claim 25, wherein the at least one sensor is affixed directly to the outer surface of the pipe.

37. The apparatus according to claim 25, wherein the at least one sensor include a multiplicity of strain sensors separated from one another by a distance d.

38. The apparatus according to claim 25, wherein the at least one sensor includes an accelerometer.

39. The apparatus according to claim 25, wherein the processor module determines a flow rate of the medium flowing in the pipe based on the information about the internal pressure changes of the medium flowing in the pipe.

40. The apparatus according to claim 25, wherein the processor module determines a composition of the medium flowing in the pipe based on the information about the internal pressure changes of the medium flowing in the pipe.

* * * * *